US008470830B2

(12) United States Patent
Ramakrishna et al.

(10) Patent No.: US 8,470,830 B2
(45) Date of Patent: *Jun. 25, 2013

(54) 5-(HETEROCYCLYL)ALKYL-N-(ARYLSUL FONYL)INDOLE COMPOUNDS AND THEIR USE AS 5-HT$_6$ LIGANDS

(75) Inventors: Venkata Satya Nirogi Ramakrishna, Hyderabad (IN); Rama Sastri Kambhampati, Hyderabad (IN); Jagadishbabu Konda, Hyderabad (IN); Prabhakar Kothmirkar, Hyderabad (IN); Venkateswarlu Jasti, Hyderabad (IN)

(73) Assignee: Suven Life Sciences Limited, Hyderabad (IN)

( * ) Notice: Subject to any disclaimer, the term of this patent is extended or adjusted under 35 U.S.C. 154(b) by 158 days.

This patent is subject to a terminal disclaimer.

(21) Appl. No.: 12/521,967

(22) PCT Filed: Jul. 26, 2007

(86) PCT No.: PCT/IN2007/000312
§ 371 (c)(1),
(2), (4) Date: Jul. 1, 2009

(87) PCT Pub. No.: WO2008/084492
PCT Pub. Date: Jul. 17, 2008

(65) Prior Publication Data
US 2010/0041673 A1 Feb. 18, 2010

(30) Foreign Application Priority Data
Jan. 8, 2007 (IN) .............................. 45/CHE/2007

(51) Int. Cl.
A61K 31/496 (2006.01)
C07D 209/08 (2006.01)
C07D 209/30 (2006.01)

(52) U.S. Cl.
USPC .................................... 514/254.09; 544/373

(58) Field of Classification Search
None
See application file for complete search history.

(56) References Cited

U.S. PATENT DOCUMENTS

| | | | | | |
|---|---|---|---|---|---|
| 5,252,584 | A | * | 10/1993 | Carling et al. ................. | 514/312 |
| 5,700,822 | A | * | 12/1997 | Hirth et al. ..................... | 514/380 |
| 7,812,017 | B2 | * | 10/2010 | Angbrant et al. .......... | 514/231.2 |
| 2004/0242589 | A1 | | 12/2004 | Bromidge et al. | |
| 2007/0060581 | A1 | | 3/2007 | Merce Vidal et al. | |

FOREIGN PATENT DOCUMENTS

| | | |
|---|---|---|
| WO | WO-9827081 A1 | 6/1998 |
| WO | WO-9902502 A2 | 1/1999 |
| WO | WO-9902502 A3 | 1/1999 |
| WO | WO-9937623 A2 | 7/1999 |
| WO | WO-9937623 A3 | 7/1999 |
| WO | WO-9942465 A2 | 8/1999 |
| WO | WO-9942465 A3 | 8/1999 |
| WO | WO-0063203 A1 | 10/2000 |
| WO | WO-0132646 A2 | 5/2001 |
| WO | WO-0236562 A2 | 5/2002 |
| WO | WO-02060871 A2 | 8/2002 |
| WO | WO-02098857 A1 | 12/2002 |
| WO | WO-02098878 A1 | 12/2002 |
| WO | WO-03013510 A1 | 2/2003 |
| WO | WO-03065046 A2 | 8/2003 |
| WO | WO-03066056 A1 | 8/2003 |
| WO | WO-03080580 A2 | 10/2003 |
| WO | WO-2004048328 A2 | 6/2004 |
| WO | WO-2004048330 A1 | 6/2004 |
| WO | WO-2004048331 A1 | 6/2004 |
| WO | WO-2004055026 A1 | 7/2004 |
| WO | WO-2005013974 A1 | 2/2005 |
| WO | 2007/020652 A1 | 2/2007 |

OTHER PUBLICATIONS

Robichaud et al. in Annual Reports in Medicinal Chemistry, vol. 36, p. 11-20 (2000).*
Rogers et al. Psychopharmacology, vol. 158, p. 114-119 (2001).*
Vippagunta et al. Advanced Drug Delivery Reviews, vol. 48, pp. 3-26 (2001).*
Bentley, Jane C., et al., "Investigation of Stretching Behaviour Induced . . . ", Br. J. of Pharmacology, 1999, pp. 1537-1542, vol. 126, Stockton Press, UK.
Berge, Stephen, et al., "Pharmaceutical Salts", Journal of Pharmaceutical Sciences, 1977, pp. 1-19, vol. 66, USA.
Bonhaus, D.W., et al., "RO438554, a High Affinity, Selective, CNS . . . ", Neuroscience 2002 Abstract, Presentation: Nov. 7, 2002, Abstract 884.5, Society for Neuroscience, USA.
Branchek, Theresa, et al., "5-HT6 Receptors as Emerging Targets . . . ", Annu. Rev. Pharmacol. Toxicol., 2000, pp. 319-334, vol. 40, Annual Reviews, USA.
Bromidge, Steven, et al "5-Chloro-N-(4-methoxy-3-piperazin-1-yl-phenyl)..",J. Med. Chem., 1999, pp. 202-205, vol. 42, American Chemical Society, USA.
Bromidge, Steven, et al., "Phenyl Benzenesulfonamides are Novel and Selective . . . ", Bioorganic & Medicinal Chemistry Letters, 2000 pp. 55-58, vol. 11, Elsevier Science, UK.
Reavill, C. and Rogers, D.C., "The Therapeutic Potential of 5-HT6 Receptor Antagonists", Current Opinion in Investigational Drugs, 2001, pp. 104-109, vol. 2, PharmaPress, UK.
Monsma, Frederick, Jr., et al., "Cloning and Expression of a Novel Serotonin . . . ", Molecular Pharmacology, 1992, pp. 320-327, vol. 43, Am. Soc. for Pharm. and Exp. Ther., USA.

(Continued)

Primary Examiner — Emily Bernhardt
(74) Attorney, Agent, or Firm — IpHorgan Ltd.

(57) ABSTRACT

Compounds including 5-(Heterocyclyl)alkyl-N-(arylsulfonyl)indole, their derivatives, their stereoisomers, their pharmaceutically acceptable salts and pharmaceutically acceptable compositions containing them and a process for the preparation of these compounds, their derivatives, their stereoisomers, their pharmaceutically acceptable salts and pharmaceutically acceptable compositions containing them. These compounds are useful in the treatment of various disorders that are related to 5-HT6 receptor functions. Specifically, the compounds of this invention are also useful in the treatment of various CNS disorders, hematological disorders, eating disorders, diseases associated with pain, respiratory diseases, genito-urological disorders, cardiovascular diseases and cancer.

21 Claims, No Drawings

OTHER PUBLICATIONS

Dawson, L.A., et al., "In Vivo Effects of the 5-HT6 Antagonist SB-271046 . . . ", Br. J. of Pharmacology, 2000, pp. 23-26, vol. 130, Macmillan Publishers, UK.

Demchyshyn, L.L., et al., "ALX-1161: Pharmacological Properties of . . . ", Neuroscience 2001 Abstract, Presentation: Nov. 12, 2001, No. 266.6, Society for Neuroscience, USA.

Ennaceur, A. and Delacour, J., "A New One-Trial Test for Neurobiological Studies . . . ",, Behavioural Brain Research, 1988, pp. 47-59, vol. 31, Elsevier Science Publishers.

Ernst, Monique, et al., "DOPA Decarboxylase Activity in Attention Deficit . . . ", J. of Neuroscience, 1998, pp. 5901-5907, vol. 18, Society for Neuroscience, USA.

Gerard, Caroline, et al., "Immuno-localization of Serotonin 5-HT6 Receptor-like . . . ", Brain Research, 1997, pp. 207-219, vol. 746, Elsevier Science.

Glennon, Richard A., et al., "2-Substituted Tryptamines: Agents with Selectivity . . . ", J. Med. Chem., 2000, pp. 1011-1018, vol. 43, American Chemical Society, USA.

Holenz, Jorg, et al., "Medicinal Chemistry Strategies to 5-HT6 Receptor Ligands . . . ", Drug Discovery Today, 2006, pp. 283-299, vol. 11, Elsevier Ltd, UK.

Kask, Ants, et al., "Neuropeptide Y Y5 Receptor Antagonist CGP71683A: the effects on food . . . ", European J. of Pharm, 2001, pp. 215-224, vol. 414, Elsevier Science, NL.

King, M.V., et al., "5-HT6 Receptor Antagonists Reverse Delay-Dependent Deficits in Novel Object . . . ", Neuropharmacology, 2004, pp. 195-204, vol. 47, Elsevier Ltd, UK.

Kohen, Ruth, et al., "Cloning, Characterization, and Chromosomal Localization . . . ", J. of Neurochemistry, 1996, pp. 47-56, vol. 66, International Society for Neurochemistry.

Lindner, Mark, et al., "An Assessment of the Effects of Serotonin 6 (5-HT6) . . . ", J. of Pharm. Exp. Ther., 2003, pp. 682-691, vol. 307, Am. Soc. for Pharm. and Exp. Ther., USA.

Mattsson, Cecilia, et al., "2-Alkyl-3-(1,2,3,6-tetrahydrophyridin-4-yl)-1H-indoles . . . ", Bioorganic & Medicinal Chemistry Letters, 2005, pp. 4230-4234, vol. 15, Elsevier Ltd.

Cole, Derek C., et al., "Approaches to the Treatment of Anxiety and Depression", Presentation, 2005, Abstract MEDI 17, 230th ACS Natl Meeting, Washington, D.C.

Monsma, Frederick J., Jr., et al, "Cloning and Expression of a Novel Serotonin . . . ", Molecular Pharmacology, 1992, pp. 320-327, vol. 43, Am. Soc. for Pharm. and Exp. Ther., USA.

Pouzet, B., et al., "Effects of the 5-HT6 Receptor Antagonist . . . ", Pharmacology Biochemistry and Behavior, 2002, pp. 635-643. vol. 71, Elsevier Science Inc.

Pullagurla, Manik R., et al, "Possible Differences in Modes of Agonist . . . ", Bioorganic & Medicinal Chemistry Letters, 2004, pp. 4569-4573, vol. 14, Elsevier Ltd.

Rogers, D.C., et al., "The Selective 5HT6 Receptor Antagonist, SB-271046-A . . . ", Abstracts, 2000, Neuroscience Research, SmithKline Beecham Pharm, UK.

Roth, Bryan L., et al., "Binding of Typical and Atypical Antipsychotic . . . ", Journ. Pharm. and Exp. Ther., 1994, pp. 1403-1410, vol. 268, Am. Soc. Pharm. and Exp. Ther., USA.

Routledge, Carol, et al., "Characterization of SB-271046: A Potent . . . ", British Journal Pharmacology, 2000, pp. 1606-1612, vol. 130, Macmillan Publishers Ltd., UK.

Ruat, Martial, et al., "A Novel Rat Serotonin (5-Ht6) Receptor . . . ", Biochemical and Biophysical Res. Commun., 1993, pp. 268-276, vol. 193, Academic Press.

Sleight, Andrew J., et al., Characterization of Ro 04-6790 and Ro 63-0563 . . . , British Journal Pharmacology, 1998, pp. 556-562, vol. 124, Stockton Press, UK.

Hirst, W.D., et al., "Characterisation of SB-399885, a Potent and Selective . . . ", Presentation, 2003, Society for Neuroscience, Washington, D.C.

Stean, Tania, et al., "Anticonvulsant Properties of the Selective 5-HT6 Receptor . . . ", Br. J. Pharm, 1999, vol. 127, Proc Suppl 131P, SmithKline Beecham Pharmaceuticals, UK.

Tsai, Yuching, et al., "N1-(Benzenesulfonyl)tryptamines as Novel 5-HT6 . . . " Bioorganic & Medicinal Chemistry Letters, 2000, pp. 2295-2299, vol. 10, Elsevier Science Ltd.

Turnbull, Andrew V., et al., "Selective Antagonism of the NPY Y5 Receptor Does Not Have . . . ", Diabetes, 2002, pp. 2441-2449, vol. 51, UK.

Ward, R.P., et al, "Localization of Serotonin Subtype 6 Receptor . . . ", Neuroscience, 1995, pp. 1105-1111, vol. 64, Elsevier Science Ltd., UK.

Woolley, M.L., et al., "A Role for 5-HT6 Receptors in Retention of Spatial . . . ", Neuropharmacology, 2001, pp. 210-219, vol. 41, Elsevier Science Ltd., UK.

Yamada, N., et al., "Improvement of Scopolamine-induced Memory Impairment . . . ", Pharmacology, Biochemistry and Behavior, 2004, pp. 787-791, vol. 78, Elsevier Inc.

Sleight, A. J., et al., Neurotransmission, 1996, vol. 11, pp. 1-5.

Sleight, A. J., et al., Serotonin ID Research Alert, 1997, vol. 2, pp. 115-118.

Mattsson, C. et al, Novel, potent and selective 2-alkyl-3-(1,2,3,6-tetrahydropyridin . . . , XVIIth International Symposium on Medicinal Chemistry, 2002.

Stadler, H., et al., "5-HT6Antagonists: A Novel Approach for the Symptomatic Treatment . . . ", 37th, IUPAC Cong. Berlin, Abstract MM-7.

Principles of Asymmetric Synthesis, J.E. Baldwin Ed., Tetrahedron series, vol. 14, pp. 311-316.

Harris et al., "Highly potent, non-basic 5-HT6 ligands. Site mutagenesis evidence for a second binding mode at 5-HT6 for antagonism" Bioorg. Medic. Chem. Letts. 20:3436-3440 (2010).

Russell et al., "N-Arylsulfonylindole Derivatives as Serotonin 5-HT6 Receptor Ligands" J. Med. Chem. 44:3881-3895 (2001).

Sikazwe et al., "Binding of Sulfonyl-Containing Arylalkylamines at Human 5-HT6 Serotonin Receptors" J. Med. Chem. 49:5217-5225 (2006).

Sleight et al., "5-HT6 and 5-HT7 receptors: molecular biology, functional correlates, and possible therapeutic indications" Drug News Perspect. 10:214-224 (1997).

Excerpts from file history of US Patent No. 7,812,017 ("Angbrant"), issued Oct. 12, 2010 by the US Patent and Trademark Office: Notice of Allowability (Jun. 2010), Applicant Arguments (May 2010), Final Rejection (Jan. 2010), Applicant Arguments (Oct. 2009), Non-Final Rejection (Apr. 2009).

Office Actions issued Mar. 6, 2012, Oct. 28, 2011, Oct. 13, 2011, Jul. 28, 2011, and Feb. 16, 2011 in U.S. Appl. No. 12/521,984.

Written Opinion issued in counterpart PCT application No. PCT/IN2007/000312 issued Jun. 26, 2008 and published Jul. 8, 2009 by the World Intellectual Property Organization website.

International Search Report issued in counterpart PCT application No. PCT/IN2007/000312 on Jun. 26, 2008.

International Preliminary Report on Patentability completed in counterpart PCT application No. PCT/IN2007/000312 on Dec. 1, 2008.

Stadler, H., et al., "5HT6Antagonists: A Novel Approach for the Symptomatic Treatment . . . ", 37th, IUPAC Cong. Berlin, Abstract MM-7.

Callahan, P. M., et al., Abst. 776.19.2004, Society for Neuroscience, 2004.

Fox, G. B., Journal of Neurochemistry, 1995, vol. 65, pp. 2796-2799.

\* cited by examiner

5-(HETEROCYCLYL)ALKYL-N-(ARYLSULFONYL)INDOLE COMPOUNDS AND THEIR USE AS 5-HT$_6$ LIGANDS

CROSS-REFERENCE TO RELATED APPLICATIONS

This is a Sect. 371 National Stage of PCT International Application No. PCT/IN2007/000321, filed on 26 Jul. 2007, claiming priority of Indian Patent Application No. 45/CHE/2007 filed on 8 Jan. 2007, the contents of both applications hereby being incorporated by reference.

FIELD OF INVENTION

The present invention relates to novel 5-(Heterocyclyl) alkyl-N-(arylsulfonyl)indole compounds of the formula (I), their derivatives, their stereoisomers, their pharmaceutically acceptable salts and pharmaceutically acceptable compositions containing them

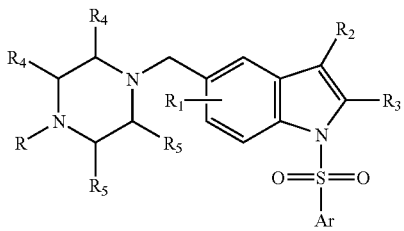

(I)

The present invention also relates to a process for the preparation of above said novel compounds, their derivatives, their stereoisomers, their pharmaceutically acceptable salts and pharmaceutically acceptable compositions containing them.

These compounds are useful in the treatment of various disorders that are related to 5-HT$_6$ receptor functions. Specifically, the compounds of this invention are also useful in the treatment of various CNS disorders, hematological disorders, eating disorders, diseases associated with pain, respiratory diseases, genito-urological disorders, cardiovascular diseases and cancer.

BACKGROUND AND PRIOR ART OF THE INVENTION

Various central nervous system disorders such as anxiety, depression, motor disorders etc., are believed to involve a disturbance of the neurotransmitter 5-hydroxytryptamine. (5-HT) or serotonin. Serotonin is localized in the central and peripheral nervous systems and is known to affect many types of conditions including psychiatric disorders, motor activity, feeding behavior, sexual activity and neuroendocrine regulation among others. 5-HT receptor subtypes regulate the various effects of serotonin. Known 5-HT receptor family includes the 5-HT$_1$, family (e.g. 5-HT$_{1A}$), the 5-HT$_2$ family (e.g. 5-HT$_{2A}$), 5-HT$_3$, 5-HT$_4$, 5-HT$_5$, 5-HT$_6$ and 5-HT$_7$ subtypes.

The 5-HT$_6$ receptor subtype was first cloned from rat tissue in 1993 (Monsma, P. J.; Shen, Y.; Ward, R. P.; Hamblin, M. W., Molecular Pharmacology, 1993, 43, 320-327) and subsequently from human tissue (Kohen, R.; Metcalf, M. A.; Khan, N.; Druck, T.; Huebner, K.; Sibley, D. R., Journal of Neurochemistry, 1996, 66, 47-56). The receptor is a G-protein coupled receptor (GPCR) positively coupled to adenylate cyclase (Ruat, M.; Traiffort, E.; Arrang, J-M.; Tardivel-Lacombe, L.; Diaz, L.; Leurs, R.; Schwartz, J-C., Biochemical Biophysical Research Communications, 1993, 193, 268-276). The receptor is found almost exclusively in the central nervous system (CNS) areas both in rats as well as in humans.

In situ hybridization studies of 5-HT$_6$ receptor in rat brain using mRNA indicate principal localization in the areas of 5-HT projection including striatum, nucleus accumbens, olfactory tubercle and hippocampal formation (Ward, R. P.; Hamblin, M. W.; Lachowicz, J. E.; Hoffman, B. J.; Sibley, D. R.; Dorsa, D. M., Neuroscience, 1995, 64, 1105-1111). Highest levels of 5-HT$_6$ receptor mRNA has been observed in the olfactory tubercle, the striatum, nucleus accumbens, dentate gyrus as well as CA$_1$, CA$_2$ and CA$_3$ regions of the hippocampus. Lower levels of 5-HT$_6$ receptor mRNA were seen in the granular layer of the cerebellum, several diencephalic nuclei, amygdala and in the cortex. Northern blots have revealed that 5-HT$_6$ receptor mRNA appears to be exclusively present in the brain, with little evidence for its presence in peripheral tissues.

The high affinity of number of antipsychotic agents towards 5-HT$_6$ receptor, the localization of its mRNA in striatum, olfactory tubercle and nucleus accumbens suggests that some of the clinical actions of these compounds may be mediated through this receptor. Its ability to bind a wide range of therapeutic compounds used in psychiatry, coupled with its intriguing distribution in the brain has stimulated significant interest in new compounds which are capable of interacting with the said receptor (Ref: Sleight, A. J. et al. (1997) 5-HT$_6$ and 5-HT$_7$ receptors: molecular biology, functional correlates and possible therapeutic indications, Drug News Perspect. 10, 214-224). Significant efforts are being made to understand the possible role of the 5-HT$_6$ receptor in psychiatry, cognitive dysfunction, motor function and control, memory, mood and the like. The compounds which demonstrate a binding affinity for the 5-HT$_6$, receptor are earnestly sought both as an aid in the study of the 5-HT$_6$ receptor and as potential therapeutic agents in the treatment of central nervous system disorders, for example see Reavill C. and Rogers D. C., Current Opinion in Investigational Drugs, 2001, 2(1): 104-109, Pharma Press Ltd.

Monsma F. J. et al. (1993) and Kohen, R. et al. (2001) have shown that several tricyclic antidepressant compounds, such as amitriptyline and atypical antidepressant compounds, such as mianserin have high affinity for the 5-HT$_6$ receptor. These findings have led to the hypothesis that the 5-HT$_6$ receptor is involved in the pathogenesis and/or treatment of affective disorders. Rodent models of anxiety-related behavior yield conflicting results about the role of the 5-HT$_6$ receptor in anxiety. Treatment with 5-HT$_6$ receptor antagonists increases seizure threshold in a rat maximal electroconvulsive-shock test [Stean, T. et al. (1999) Anticonvulsant properties of the selective 5-HT$_6$ receptor antagonist SB-271046 in the rat maximal electroshock seizure threshold test. Br. J. Pharmacol. 127, 131P; Routledge, C. et al. (2000) Characterization of SB-271046: a potent, selective and orally active 5-HT$_6$) receptor antagonist. Br. J. Pharmacol. 130, 1606-1612]. Although this indicates that 5-HT$_6$ receptors might regulate seizure threshold, the effect is not as pronounced as that of known anticonvulsant drugs.

Our understanding of the roles of 5-HT$_6$ receptor ligands is most advanced in two therapeutic indications in which this receptor is likely to have a major role: learning and memory deficits and abnormal feeding behaviour. The exact role of the 5-HT$_6$ receptor is yet to be established in other CNS indications such as anxiety; although one 5-HT$_6$ agonist has reached Phase I clinical trials recently, the exact role of the receptor is still to be established and is the focus of significant investigation. There are many potential therapeutic uses for 5-HT$_6$ receptor ligands in humans based on direct effects and on indications from available scientific studies. These studies include the localization of the receptor, the affinity of ligands with known in-vivo activity and various animal studies conducted so far. Preferably, antagonist compounds of 5-HT$_6$ receptors are sought after as therapeutic agents.

One potential therapeutic use of modulators of 5-HT$_6$ receptor functions is in the enhancement of cognition and memory in human diseases such as Alzheimer's. The high levels of receptor found in structures such as the forebrain, including the caudate/putamen, hippocampus, nucleus accumbens and cortex suggests a role for the receptor in memory and cognition since these areas are known to play a vital role in memory (Gerard, C.; Martres, M. P.; Lefevre, K.; Miquel, M. C.; Verge, D.; Lanfumey, R.; Doucet, E.; Danon, M.; E I Mestikawy, S., Brain Research, 1997, 746, 207-219). The ability of known 5-HT$_6$ receptor ligands to enhance cholinergic transmission also supports the potential cognition use (Bentey, J. C.; Boursson, A.; Boess, F. G.; Kone, F. C.; Marsden, C. A.; Petit N.; Sleight, A. J., British Journal of Pharmacology, 1999, 126 (7), 1537-1542).

Studies have found that a known 5-HT$_6$ selective antagonist significantly increased glutamate and aspartate levels in the frontal cortex without elevating levels of noradrenaline, dopamine or 5-HT. This selective elevation of certain neurochemicals is noted during memory and cognition, strongly suggests a role for 5-HT$_6$ ligands in cognition (Dawson, L. A.; Nguyen, H. Q.; Li, P. British Journal of Pharmacology, 2000, 130 (1), 23-26). Animal studies of memory and learning with a known selective 5-HT$_6$ antagonist has some positive effects (Rogers, D. C.; Hatcher, P. D.; Hagan, J. J. Society of Neuroscience, Abstracts, 2000, 26, 680).

A related potential therapeutic use for 5-HT$_6$ ligands is in the treatment of attention deficit disorders (ADD, also known as Attention Deficit Hyperactivity Disorder or ADHD) in children as well as adults. As 5-HT$_6$ antagonists appear to enhance the activity of the nigrostriatal dopamine pathway and ADHD has been linked to abnormalities in the caudate (Ernst, M; Zametkin, A. J.; Matochik, J. H.; Jons, P. A.; Cohen, R. M., Journal of Neuroscience, 1998, 18(15), 5901-5907), 5-HT$_6$ antagonists may attenuate attention deficit disorders.

At present, a few fully selective agonists are available. The Wyeth agonist WAY-181187 is currently in Phase I trials to target anxiety [Cole, D. C. et al. (2005) Discovery of a potent, selective and orally active 5-HT$_6$ receptor agonist, WAY-181187. 230th ACS Natl. Meet. (August 28-September 1, Washington D.C.), Abstract MEDI 17.]

International Patent Publication WO 03/066056 A1 reports that antagonism of 5-HT$_6$ receptor could promote neuronal growth within the central nervous system of a mammal. Another International Patent Publication WO 03/065046 A2 discloses new variant of human 5-HT$_6$ receptor and proposes that 5-HT$_6$ receptor is associated with numerous other disorders.

Early studies examining the affinity of various CNS ligands with known therapeutic utility or a strong structural resemblance to known drugs suggests a role for 5-HT$_6$ ligands in the treatment of schizophrenia and depression. For example, clozapine (an effective clinical antipsychotic) has high affinity for the 5-HT$_6$ receptor subtype. Also, several clinical antidepressants have high affinity for the receptor as well and act as antagonists at this site (Branchek, T. A.; Blackburn, T. P., Annual Reviews in Pharmacology and Toxicology, 2000, 40, 319-334).

Further, recent in-vivo studies in rats indicate that 5-HT$_6$ modulators may be useful in the treatment of movement disorders including epilepsy (Stean, T.; Routledge, C.; Upton, N., British Journal of Pharmacology, 1999, 127 Proc. Supplement-131P; and Routledge, C.; Bromidge, S. M.; Moss, S. F.; Price, G. W.; Hirst, W.; Newman, H.; Riley, G.; Gager, T.; Stean, T.; Upton, N.; Clarke, S. E.; Brown, A. M., British Journal of Pharmacology, 2000, 30 (7), 1606-1612).

Taken together, the above studies strongly suggest that compounds which are 5-HT$_6$ receptor modulators, i.e. ligands, may be useful for therapeutic indications including, the treatment of diseases associated with a deficit in memory, cognition and learning such as Alzheimer's and attention deficit disorder; the treatment of personality disorders such as schizophrenia; the treatment of behavioral disorders, e.g. anxiety, depression and obsessive compulsive disorders; the treatment of motion or motor disorders such as Parkinson's disease and epilepsy; the treatment of diseases associated with neurodegeneration such as stroke or head trauma; or withdrawal from drug addiction including addiction to nicotine, alcohol and other substances of abuse.

Such compounds are also expected to be of use in the treatment of certain gastrointestinal (GI) disorders such as functional bowel disorder. See for example, Roth, B. L.; et al., Journal of Pharmacology and Experimental Therapeutics, 1994, 268, pages 1403-1412; Sibley, D. R.; et al., Molecular Pharmacology, 1993, 43, 320-327, Sleight, A. J.; et al., Neurotransmission, 1995, 11, 1-5; and Sleight, A. J.; et al., Serotonin ID Research Alert, 1997, 2(3), 115-118.

Furthermore, the effect of 5-HT$_6$ antagonist and 5-HT$_6$ antisense oligonucleotides to reduce food intake in rats has been reported, thus potentially in treatment of obesity. See for example, Bentey, J. C.; Boursson, A.; Boess, F. G.; Kone, F. C.; Marsden, C. A.; Petit, N.; Sleight, A. J., British Journal of Pharmacology, 1999, 126 (7), 1537-1542); Wooley et al., Neuropharmacology, 2001, 41: 210-129; and WO 02/098878.

Recently a review by Holenz, Jo"rg and et. al., Drug Discovery Today, 11, 7/8, April 2006, Medicinal chemistry strategies to 5-HT$_6$ receptor ligands as potential cognitive enhancers and antiobesity agents, gives elaborate discussion on evolution of 5-HT$_6$ ligands. It had summarized pharmacological tools and preclinical candidates used in evaluation of 5-HT$_6$ receptor in illnesses such as schizophrenia, other dopamine-related disorders and depression and to profile the neurochemical and electrophysiological effects of either blockade or activation of 5-HT$_6$ receptors. Furthermore, they have been used to characterize the 5-HT$_6$ receptor and to investigate its distribution.

So far several clinical candidates form the part of indole-type structures and are closely related structurally to the endogenous ligand 5-HT, for example compounds by Glennon, R. A. et al. 2-Substituted tryptamines: agents with selectivity for 5-HT$_6$ serotonin receptors, J. Med. Chem. 43, 1011-1018, 2000; Tsai, Y. et al. N1-(Benzenesulfonyl)tryptamines as novel 5-HT$_6$ antagonists, Bioorg. Med. Chem. Lett. 10, 2295-2299, 2000; Demchyshyn L. et al., ALX-1161: pharmacological properties of a potent and selective 5-HT$_6$ receptor antagonist, 31st Annu. Meet. Soc. Neurosci. (November 10-15), Abstract 266.6, 2001; Slassi, A. et al. Preparation of 1-(arylsulfonyl)-3-(tetrahydropyridinyl)indoles as 5-HT$_6$ receptor inhibitors, WO 200063203, 2000; Mattsson, C. et al., Novel, potent and selective 2-alkyl-3-(1,2,3,6-tetrahydropyridin-4-yl)-1H-indole as 5-HT$_6$ receptor agonists, XVIIth International Symposium on Medicinal Chemistry, 2002; Mattsson, C. et al., 2-Alkyl-3-(1,2,3,6-tetrahydropyridin-4-yl)-1H-indoles as novel 5-HT$_6$ receptor agonists, Bioorg. Med. Chem. Lett. 15, 4230-4234, 2005]

Structure functionality relationships are described in the section on indole-like structures (and in a receptor-modeling study in which Pullagurla et al. claim different binding sites for agonists and antagonists [Pullagurla, M. R. et al. (2004) Possible differences in modes of agonist and antagonist binding at human 5-HT$_6$ receptors. Bioorg. Med. Chem. Lett. 14, 4569-4573]. Most antagonists that are reported form part of the monocyclic, bicyclic and tricyclic aryl-piperazine classes (Bromidge, S. M. et al. (1999) 5-Chloro-N-(4-methoxy-3-piperazin-1-ylphenyl)-3-methyl-2-benzothiophenesulfonamide (SB-271046): A potent, selective and orally bioavailable 5-HT$_6$ receptor antagonist. J. Med. Chem. 42, 202-205; Bromidge, S. M. et al. (2001) Phenyl benzenesulfonamides are novel and selective 5-HT$_6$ antagonists: Identification of N-(2,5-dibromo-3-fluorophenyl)-4-methoxy-3-piperazin-1-ylbenzenesulfonamide (SB-357134). Bioorg. Med. Chem. Lett 11, 55-58; Hirst, W. D. et al. (2003) Characterisation of SB-399885, a potent and selective 5-HT$_6$ receptor antagonist. 33$^{rd}$ Annu. Meet. Soc. Neurosci. (November 8-12, New Orleans), Abstract 576.7; Stadler, H. et al. (1999) 5-HT$_6$ antagonists: A novel approach for the symptomatic treatment of Alzheimer's disease. 37$^{th}$ IUPAC Cong. Berlin, Abstract MM-7; Bonhaus, D. W. et al. (2002) Ro-4368554, a high affinity, selective, CNS penetrating 5-HT$_6$ receptor antagonist. 32$^{nd}$ Annu. Meet. Soc. Neurosci., Abstract 884.5.; Beard, C. C. et al. (2002) Preparation of new indole derivatives with 5-HT$_6$ receptor affinity. WO patent 2002098857].

Ro 63-0563: Potent and selective antagonists at human and rat 5-HT$_6$ receptors. Br. J. Pharmacol. 124, (556-562). Phase II antagonist candidate from GlaxoSmithKline, SB-742457 for the therapeutic indication of cognitive dysfunction associated with Alzheimer's disease [Ahmed, M. et al. (2003) Novel compounds. WO patent 2003080580], and the Lilly compound LY483518 [Filla, S. A. et al. (2002) Preparation of benzenesulfonic acid indol-5-yl esters as antagonists of the 5-HT$_6$ receptor. WO 2002060871]. SB-271046, the first 5-HT$_6$ receptor antagonist to enter Phase I clinical development, has been discontinued (probably because of low penetration of the blood-brain barrier). In addition, the selective 5-HT$_6$ receptor antagonist SB-271046 is inactive in animal tests related to either positive or negative symptoms of schizophrenia [Pouzet, B. et al. (2002) Effects of the 5-HT$_6$ receptor antagonist, SB-271046, in animal models for schizophrenia. Pharmacol. Biochem. Behav. 71, 635-643].

International Patent Publications WO 2004/055026 A1, WO 2004/048331 A1, WO 2004/048330 A1 and WO 2004/048328 A2 (all assigned to Suven Life Sciences Limited) describe the related prior art. Further WO 98/27081, WO 99/02502, WO 99/37623, WO 99/42465 and WO 01/32646 (all assigned to Glaxo SmithKline Beecham PLC) disclose a series of aryl sulphonamide and sulphoxide compounds as 5-HT$_6$ receptor antagonists and are claimed to be useful in the treatment of various CNS disorders. While some 5-HT$_6$ modulators have been disclosed, there continues to be a need for compounds that are useful for modulating 5-HT$_6$. Surprisingly, it has been found that 5-(Heterocyclyl) alkyl-N-(arylsulfonyl)indole compounds of formula (I) demonstrate very high 5-HT$_6$ receptor affinity. Therefore, it is an object of this invention to provide compounds, which are useful as therapeutic agents in the treatment of a variety of central nervous system disorders or disorders affected by the 5-HT$_6$ receptor.

SUMMARY OF THE INVENTION

The present invention relates to novel 5-Heterocyclylalkyl-N-(arylsulfonyl)indole compounds, of the general formula (I), their derivatives, their stereoisomers, their pharmaceutically acceptable salts and pharmaceutically acceptable compositions containing them.

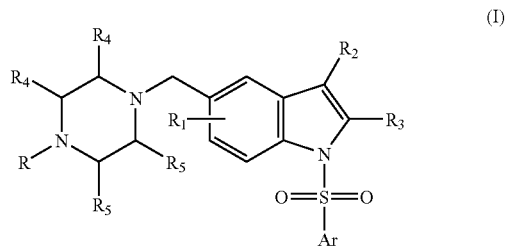

(I)

wherein Ar represents phenyl, naphthyl, monocyclic or bicyclic rings, which may be substituted by one or more independent substituents selected from $R_1$.

$R_1$ represents one or more independent substituents selected from hydrogen, halogen, ($C_1$-$C_3$)alkyl, halo($C_1$-$C_3$) alkyl, ($C_1$-$C_3$)alkoxy, halo($C_1$-$C_3$)alkoxy, alkyl thio, cyclo ($C_3$-$C_6$)alkyl or cyclo($C_3$-$C_6$)alkoxy;

$R_2$ represents hydrogen, halogen, ($C_1$-$C_3$)alkyl, halo($C_1$-$C_3$)alkyl, ($C_1$-$C_3$)alkoxy or halo ($C_1$-$C_3$)alkoxy;

$R_3$ represents hydrogen, halogen, ($C_1$-$C_3$) alkyl or halo($C_1$-$C_3$)alkyl, ($C_1$-$C_3$)alkoxy or halo($C_1$-$C_3$)alkoxy;

R represents hydrogen atom, ($C_1$-$C_3$) alkyl or halo ($C_1$-$C_3$) alkyl group;

$R_4$ and $R_5$ represent hydrogen, halogen, ($C_1$-$C_3$) alkyl or halo($C_1$-$C_3$)alkyl, ($C_1$-$C_3$)alkoxy or halo($C_1$-$C_3$)alkoxy;

The present invention relates to use of a therapeutically effective amount of compound of formula (I), to manufacture a medicament, in the treatment or prevention of a disorder involving selective affinity for the 5-HT$_6$ receptor.

Specifically, the compounds of this invention are also useful in the treatment of various CNS disorders, hematological disorders, eating disorders, diseases associated with pain, respiratory diseases, genito-urological disorders, cardiovascular diseases and cancer.

In another aspect, the invention relates to pharmaceutical compositions containing a therapeutically effective amount of at least one compound of formula (I), or individual stereoisomers, racemic or non-racemic mixture of stereoisomers, or pharmaceutically acceptable salts or solvates thereof, in admixture with at least one suitable carrier.

In another aspect, the invention relates to compositions comprising and methods for using compounds of Formula (I).

In still another aspect, the invention relates to the use of a therapeutically effective amount of compound of formula (I), to manufacture a medicament, in the treatment or prevention of a disorder involving selective affinity for the 5-HT$_6$ receptor.

In yet another aspect, the invention further relates to the process for preparing compounds of formula (I).

Following is the partial list of the compounds belonging to general formula (I):

1-Benzenesulfonyl-5-(4-methylpiperazin-1-yl methyl)-1H-indole dihydrochloride;

1-(4-Methylbenzenesulfonyl)-5-(4-methylpiperazin-1-yl methyl)-1H-indole;
1-(4-Fluorobenzenesulfonyl)-5-(4-methylpiperazin-1-yl methyl)-1H-indole;
1-(4-Methoxybenzenesulfonyl)-5-(4-Methylpiperazin-1-yl methyl)-1H-indole;
1-[4-(1-Methylethyl)benzenesulfonyl]-5-(4-methylpiperazin-1-yl methyl)-1H-indole;
1-(4-Chlorobenzenesulfonyl)-5-(4-ethylpiperazin-1-yl methyl)-1H-indole dihydrochloride;
1-(4-Fluorobenzenesulfonyl)-5-(4-ethylpiperazin-yl methyl)-1H-indole dihydrochloride;
1-(4-Methylethyl)benzenesulfonyl]-5-(4-ethylpiperazin-1-yl methyl)-1H-indole dihydrochloride;
1-(4-Methoxybenzenesulfonyl)-5-(4-ethylpiperazin-1-yl methyl)-1H-indole dihydrochloride;
1-(2,4-Difluorobenzenesulfonyl)-5-(4-ethylpiperazin-1-yl methyl)-1H-indole dihydrochloride;
1-(4-Bromobenzenesulfonyl)-5-(4-ethylpiperazin-1-yl methyl)-1H-indole dihydrochloride;
1-(3-Trifluoromethylbenzenesulfonyl)-5-(4-ethylpiperazin-1-yl methyl)-1H-indole dihydrochloride;
1-(4-Methylbenzenesulfonyl)-5-(4-ethylpiperazin-1-yl methyl)-1H-indole dihydrochloride;
1-(2,3-Dichlorobenzenesulfonyl)-5-(4-ethylpiperazin-1-yl methyl)-1H-indole dihydrochloride;
1-(2-Bromobenzenesulfonyl)-5-(4-ethylpiperazin-1-yl methyl)-1H-indole dihydrochloride;
1-(4-Chlorobenzenesulfonyl)-5-(4-ethylpiperazin-1-yl methyl)-3-bromo-1H-indole dihydrochloride;
1-Benzenesulfonyl-5-(4-Ethylpiperazin-1-yl methyl)-1H-indole dihydrochloride;
1-(2,4-Difluorobenzenesulfonyl)-5-(4-methylpiperazin-1-yl methyl)-1H-Indole;
1-(2-Chloro-5-trifluoromethylbenzenesulfonyl)-5-(4-methylpiperazin-1-yl methyl)-1H-indole;
1-(2-Bromobenzenesulfonyl)-5-(4-methylpiperazin-1-yl methyl)-1H-indole;
1-(2,3-Dichlorobenzenesulfonyl)-5-(4-methylpiperazin-1-yl methyl)-1H-indole;
1-(4-Chlorobenzenesulfonyl)-5-(4-methylpiperazin-1-yl methyl)-1H-indole;
1-(3-Trifluoromethylbenzenesulfonyl)-5-(4-methylpiperazin-1-yl methyl)-1H-indole dihydrochloride;
1-(4-Chlorobenzenesulfonyl)-3-chloro-5-(4-methylpiperazin-1-yl methyl)-1H-indole;
1-(4-Fluorobenzenesulfonyl)-3-chloro-5-(4-methylpiperazin-1-yl methyl)-1H-indole;
1-(2,4-Difluorobenzenesulfonyl)-3-chloro-5-(4-methylpiperazin-1-yl methyl)-1H-indole dihydrochloride;
1-(2-Chloro-5-trifluoromethylbenzenesulfonyl)-3-chloro-5-(4-methylpiperazin-1-yl methyl)-1H-indole dihydrochloride;
1-(4-Fluorobenzenesulfonyl)-4-isopropoxy-5-(4-methylpiperazin-1-yl methyl)-1H-indole;
1-[4-(1-Methylethyl)benzenesulfonyl]-4-isopropoxy-5-(4-methylpiperazin-1-yl methyl)-1H-indole;
1-(4-Fluorobenzenesulfonyl)-3-chloro-5-(piperazin-1-yl methyl)-1H-indole dihydrochloride;
1-(2-Bromobenzenesulfonyl)-5-(piperazin-1-yl methyl)-1H-indole dihydrochloride;
1-(2-Difluorobenzenesulfonyl)-3-chloro-5-(piperazin-1-yl methyl)-1H-indole dihydrochloride;
1-(Benzenesulfonyl)-5-(piperazin-1-yl methyl)-1H-indole dihydrochloride,
1-[4-(1-Methylethyl)benzenesulfonyl]-5-(piperazin-1-yl methyl)-1H-indole dihydrochloride;
1-(3-Chloro benzenesulfonyl-5-(2,4-dimethyl piperazin-1-yl methyl)-1H-indole;
2-Chloro-5-(4-methyl piperazin-1-yl methyl)-1-(3-methyl benzenesulfonyl)-1H-indole;
2-Methoxy-5-(4-methyl piperazin-1-yl methyl)-1-(3-methyl benzenesulfonyl)-1H-indole;
1-(3-Chloro benzenesulfonyl)-3-methoxy-5-(4-methyl piperazin-1-yl methyl)-1H-indole;
5-(4-Methyl piperazin-1-yl methyl)-1-(4-methyl benzenesulfonyl)-6-trifluoromethyl-1H-indole;
1-(3-Chloro benzenesulfonyl)-7-methoxy-5-(4-methyl piperazin-1-yl methyl)-1H-indole;
a stereoisomer thereof; and a salt thereof.

DETAILED DESCRIPTION OF THE INVENTION

Unless otherwise stated, the following terms used in the specification and claims have the meanings given below:

"Halogen" means fluorine, chlorine, bromine or iodine.

"$(C_1-C_3)$alkyl" means straight or branched chain alkyl radicals containing one to three carbon atoms and include methyl, ethyl, n-propyl and iso-propyl.

"$(C_1-C_3)$alkoxy" means straight or branched chain alkyl radicals containing one to three carbon atoms and include methoxy, ethoxy, propyloxy and iso-propyloxy.

"Halo$(C_1-C_3)$alkyl" means straight or branched chain alkyl radicals containing one to three carbon atoms and include fluoromethyl, difluoromethyl, trifluoromethyl, trifluoroethyl, fluoroethyl, difluoroethyl and the like.

"Halo$(C_1-C_3)$alkoxy" means straight or branched chain alkyl radicals containing one to three carbon atoms and include fluoromethoxy, difluoromethoxy, trifluoromethoxy, trifluoroethoxy, fluoroethoxy, difluoroethoxy and the like.

"Alkyl Thio" means straight or branched chain alkyl radicals containing one to three carbon atoms and include methyl thio, ethyl thio, propyl thio, isopropyl thio and the like.

"Cyclo$(C_3-C_6)$alkyl" means cyclic alkyl radicals containing three to six carbon atoms and include cyclopropyl, cyclobutyl, cyclopentyl or cyclohexyl.

"Cyclo$(C_3-C_6)$alkoxy" means cyclic alkyl radicals containing three to six carbon atoms and include cyclopropyloxy, cyclobutyloxy, cyclopentyloxy or cyclohexyloxy.

"Monocyclic or Bicyclic ring system" is intended to mean both heteroaryl and heterocyclic rings.

"Heteroaryl" means 5 to 6 membered monocyclic aromatic ring or fused 8 to 10 membered bicyclic aromatic rings containing 1 to 3 heteroatoms selected from oxygen, nitrogen and sulphur. Suitable examples of monocyclic aromatic rings include thienyl, furyl, pyrrolyl, triazolyl, imidazolyl, oxazolyl, thiazolyl, oxadiazolyl, isothiazolyl, isoxazolyl, thiadiazolyl, pyrazolyl, pyrimidinyl, pyridazinyl, pyrazinyl and pyridyl. Suitable examples of fused aromatic rings include benzofused aromatic rings such as quinolinyl, isoquinolinyl, quinazolinyl quinoxalinyl, cinnolinyl, naphthyridinyl, indolyl, isoindolyl, indazolyl, pyrrolopyridinyl, benzofuranyl, isobenzofuranyl, benzothienyl, benzimidazolyl, benzoxazolyl, benzisoxazolyl, benzothiazolyl, benzisothiazolyl, benzoxadiazolyl, benzothiadiazolyl, benzotriazolyl and the like. Heteroaryl groups, as described above, may be linked to the remainder of the molecule via a carbon atom or, when present, a suitable nitrogen atom except where otherwise indicated above.

"Heterocyclic ring" means 5 to 7 membered non-aromatic ring containing 1 to 3 heteroatoms selected from oxygen, nitrogen and sulphur. Such rings may be partially unsaturated. Suitable examples of heterocyclic rings include piperidinyl, tetrahydropyridinyl, pyrrolidinyl, morpholinyl, azepanyl, diazepanyl and piperazinyl. 5 to 7 membered heterocyclic ring, as described above, may be linked to the remainder of the molecule via a carbon atom or a suitable nitrogen atom.

The term "schizophrenia" means schizophrenia, schizophreniform, disorder, schizoaffective disorder and psychotic disorder wherein the term "psychotic" refers to delusions, prominent hallucinations, disorganized speech or disorganized or catatonic behavior. See Diagnostic and Statistical Manual of Mental Disorder, fourth edition, American Psychiatric Association, Washington, D.C.

The phrase "pharmaceutically acceptable" indicates that the substance or composition must be compatible chemically and/or toxicologically, with the other ingredients comprising a formulation, the mammal being treated therewith.

"Therapeutically effective amount" is defined as 'an amount of a compound of the present invention that (i) treats or prevents the particular disease, condition or disorder (ii) attenuates, ameliorates or eliminates one or more symptoms of the particular disease, condition or disorder (iii) prevents or delays the onset of one or more symptoms of the particular disease, condition or disorder described herein'.

The terms "treating", "treat" or "treatment" embrace all the meanings such as preventative, prophylactic and palliative.

The term "stereoisomers" is a general term for all isomers of the individual molecules that differ only in the orientation of their atoms in space. It includes mirror image isomers (enantiomers), geometric (cis-trans) isomers and isomers of compounds with more than one chiral centre that are not mirror images of one another (diastereomers).

Certain compounds of formula (I) are capable of existing in stereoisomeric forms (e.g. diastereomers and enantiomers) and the invention extends to each of these stereo isomeric forms and to mixtures thereof including racemates. The different stereoisomeric forms may be separated from one another by the usual methods or any given isomer may be obtained by stereospecific or asymmetric synthesis. The invention also extends to tautomeric forms and mixtures thereof.

The stereoisomers as a rule are generally obtained as racemates that can be separated into the optically active isomers in a manner known per se. In the case of the compounds of general formula (I) having an asymmetric carbon atom the present invention relates to the D-form, the L-form and D,L-mixtures and in the case of a number of asymmetric carbon atoms, the diastereomeric forms and the invention extends to each of these stereoisomeric forms and to mixtures thereof including racemates. Those compounds of general formula (I), which have an asymmetric carbon, and as a rule are obtained as racemates can be separated from one another by the usual methods, or any given isomer may be obtained by stereospecific or asymmetric synthesis. However, it is also possible to employ an optically active compound from the start, a correspondingly optically active enantiomeric or diastereomeric compound then being obtained as the final compound.

The stereoisomers of compounds of general formula (I) may be prepared by one or more ways presented below:
i) One or more of the reagents may be used in their optically active form.
ii) Optically pure catalyst or chiral ligands along with metal catalyst may be employed in the reduction process. The metal catalyst may be Rhodium, Ruthenium, Indium and the like. The chiral ligands may preferably be chiral phosphines (Principles of Asymmetric synthesis, 3. E, Baldwin Ed., Tetrahedron series, 14, 311-316).
iii) The mixture of stereoisomers may be resolved by conventional methods such as forming diastereomeric salts with chiral acids or chiral amines, or chiral amino alcohols, chiral amino acids. The resulting mixture of diastereomers may then be separated by methods such as fractional crystallization, chromatography and the like, which is followed by an additional step of isolating the optically active product by hydrolyzing the derivative (Jacques et. al., "Enantiomers, Racemates and Resolution", Wiley Interscience, 1981).
iv) The mixture of stereoisomers may be resolved by conventional methods such as microbial resolution, resolving the diastereomeric salts formed with chiral acids or chiral bases.

Chiral acids that can be employed may be tartaric acid, mandelic acid, lactic acid, camphorsulfonic acid, amino acids and the like. Chiral bases that can be employed may be cinchona alkaloids, brucine or a basic amino acid such as lysine, arginine and the like. In the case of the compounds of general formula (I) containing geometric isomerism the present invention relates to all of these geometric isomers.

Suitable pharmaceutically acceptable salts will be apparent to those skilled in the art and include those described in J. Pharm. Sci., 1977, 66, 1-19, such as acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid. The present invention includes, within its scope, all possible stoichiometric and non-stoichiometric forms.

The pharmaceutically acceptable salts forming a part of this invention may be prepared by treating the compound of formula (I) with 1-6 equivalents of a base such as sodium hydride, sodium methoxide, sodium ethoxide, sodium hydroxide, potassium t-butoxide, calcium hydroxide, calcium acetate, calcium chloride, magnesium hydroxide, magnesium chloride and the like. Solvents such as water, acetone, ether, THF, methanol, ethanol, t-butanol, dioxane, isopropanol, isopropyl ether or mixtures thereof may be used.

In addition to pharmaceutically acceptable salts, other salts are included in the invention. They may serve as intermediates in the purification of the compounds, in the preparation of other salts, or in the identification and characterization of the compounds or intermediates.

The compounds of formula (I) may be prepared in crystalline or non-crystalline form, and, if crystalline, may optionally be solvated, eg. as the hydrate. This invention includes within its scope stoichiometric solvates (eg. hydrates) as well as compounds containing variable amounts of solvent (eg. water).

The present invention also provides a process for the preparation of a compound of formula (I) or a pharmaceutically acceptable salt thereof, which comprises of the following route, wherein the key intermediate is synthesized by various methods known in literature.

Scheme-I

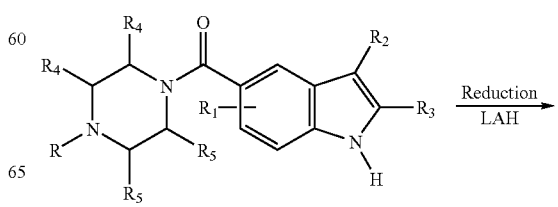

-continued

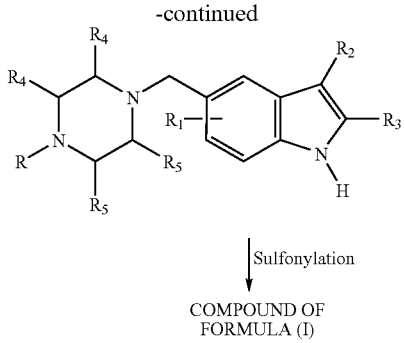

↓ Sulfonylation

COMPOUND OF
FORMULA (I)

The process of this invention includes contacting a compound of the following formula (a),

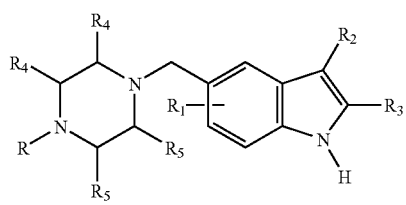

(a)

Wherein all substitutents are as described earlier, with aryl sulfonyl compound of formula (ArSO$_2$Cl), wherein Ar is as defined for the compounds of formula (I), in presence of inert solvent and appropriate base at suitable temperature to obtain a compound of formula (I); which if required may be derivatized further. Our previous patent application WO 2004/048330 A1 gives more details on the reaction conditions and reagents useful in the said interconversions of the compounds of formula (I).

The reaction of indole derivative with aryl sulfonyl chlorides (ArSO$_2$Cl), can take place in the presence of an inert organic solvent which includes, aromatic hydrocarbons such as toluene, o-, m-, p-xylene; halogenated hydrocarbons such as methylene chloride, chloroform and chlorobenzene; ethers such as diethyl ether, diphenyl ether, disopropyl ether, tert-butyl methyl ether, dioxane, anisole and tetrahydrofuran; nitriles such as acetonitrile and propionitrile; alcohols such as methanol, ethanol, n-propranol, n-butanol, tert-butanol and also DMF (N,N-dimethylformamide), DMSO(N,N-dimethyl sulfoxide) and water. The preferred list of solvents include DMSO, DMF, acetonitrile and THF. Mixtures of these in varying ratios can also be used. Suitable bases are, generally, inorganic compounds such as alkali metal hydroxides and alkaline earth metal hydroxides, such as lithium hydroxide, sodium hydroxide, potassium hydroxide and calcium hydroxide; alkali metal oxides and alkaline earth metal oxides, such as lithium oxide, sodium oxide, magnesium oxide and calcium oxide; alkali metal hydrides and alkaline earth metal hydrides such as lithium hydride, sodium hydride, potassium hydride and calcium hydride; alkali metal amides and alkaline earth metal amides such as lithium amide, sodium amide, potassium amide and calcium amide; alkali metal carbonates and alkaline earth metal carbonates such as lithium carbonate and calcium carbonate; and also alkali metal hydrogen carbonates and alkaline earth metal hydrogen carbonates such as sodium hydrogen carbonate; organometallic compounds, particularly alkali-metal alkyls such as methyl lithium, butyl lithium, phenyl lithium; alkyl magnesium halides such as methyl magnesium chloride and alkali metal alkoxides and alkaline earth metal alkoxides such as sodium methoxide, sodium ethoxide, potassium ethoxide, potassium tert-butoxide and di-methoxymagnesium, further more organic bases e.g. triethylamine, triisopropylamine, N-methylpiperidine and pyridine. Sodium hydroxide, sodium methoxide, sodium ethoxide, potassium hydroxide potassium carbonate and triethylamine are especially preferred. Suitably the reaction may be effected in the presence of phase transfer catalyst such as tetra-n-butylammonium hydrogensulphate and the like. The inert atmosphere may be maintained by using inert gases such as N$_2$, Ar or He, the duration of the reaction can be maintained in the range of 1 to 24 hours, preferably 2 to 6 hours. If desired the resulting compound is converted into a salt thereof.

Compounds obtained by the above method of preparation of the present invention can be transformed into another compound of this invention by further chemical modifications using well known reactions such as oxidation, reduction, protection, deprotection, rearrangement reaction, halogenation, hydroxylation, alkylation, alkylthiolation, demethylation, O-alkylation, O-acylation, N-alkylation, N-alkenylation, N-acylation, N-cyanation, N-sulfonylation, coupling reaction using transition metals and the like.

If necessary, any one or more than one of the following steps can be carried out,
 i) Converting a compound of the formula (I) into another compound of the formula (I)
 ii) Removing any protecting groups; or
 iii) Forming a pharmaceutically acceptable salt, solvate or a prodrug thereof.

Process (i) may be performed using conventional interconversion procedures such as epimerisation, oxidation, reduction, alkylation, nucleophilic or electrophilic aromatic substitution, and ester hydrolysis or amide bond formation.

In process (ii) examples of protecting groups and the means for their removal can be found in T. W. Greene 'Protective Groups in Organic Synthesis' (J. Wiley and Sons, 1991). Suitable amine protecting groups include sulphonyl (e.g. tosyl), acyl (e.g. acetyl, 2', 2', 2'-trichloroethoxycarbonyl, benzyloxycarbonyl or t-butoxycarbonyl) and arylalkyl (eg. benzyl), which may be removed by hydrolysis (e.g. using an acid such as hydrochloric or trifluoroacetic acid) or reductively (e.g. hydrogenolysis of a benzyl group or reductive removal of a 2', 2', 2'-trichloroethoxycarbonyl group using zinc in acetic acid) as appropriate. Other suitable amine protecting groups include trifluoroacetyl, which may be removed by base catalysed hydrolysis or a solid phase resin bound benzyl group, such as a Merrifield resin bound 2,6-dimethoxybenzyl group (Ellman linker), which may be removed by acid catalyzed hydrolysis, for example with trifluoroacetic acid.

In process (iii) halogenation, hydroxylation, alkylation and/or pharmaceutically acceptable salts may be prepared conventionally by reaction with the appropriate acid or acid derivative as described earlier in detail.

In order to use the compounds of formula (I) in therapy, they will normally be formulated into a pharmaceutical composition in accordance with standard pharmaceutical practice.

The pharmaceutical compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or a form suitable for administration by inhalation or insufflation.

For oral administration, the pharmaceutical compositions may take the form of for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol) and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampoules or in multi-dose containers, with an added preservative. The compositions may take such forms as suspensions, solutions or emulsions in oily or aqueous vehicles and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of an aerosol spray from a pressurized container or a nebulizer or from a capsule using a inhaler or insufflator. In the case of a pressurized aerosol, a suitable propellant, e.g., dichlorodifluoromethane, trichlorofluoromethane, dichlorotetrafluoroethane, carbon dioxide or other suitable gas and the dosage unit may be determined by providing a valve to deliver a metered amount. The medicament for pressurized container or nebulizer may contain a solution or suspension of the active compound while for a capsule; it preferably should be in the form of powder. Capsules and cartridges (made, for example, from gelatin) for use in an inhaler or insufflator may be formulated containing a powder mix of a compound of the invention and a suitable powder base such as lactose or starch.

Aerosol formulations for treatment of the conditions referred to above (e.g., migraine) in the average adult human are preferably arranged so that each metered dose or "puff" of aerosol contains 20 µg to 1000 µg of the compound of the invention. The overall daily dose with an aerosol will be within the range 100 µg to 10 mg. Administration may be several times daily, for example 2, 3, 4 or 8 times, giving for example, 1, 2 or 3 doses each time.

An effective amount of a compound of general formula (I) or their derivatives as defined above can be used to produce a medicament along with conventional pharmaceutical auxiliaries, carriers and additives.

Such therapy includes multiple choices: for example, administering two compatible compounds simultaneously in a single dose form or administering each compound individually in a separate dosage; or if required at same time interval or separately in order to maximize the beneficial effect or minimize the potential side-effects of the drugs according to the known principles of pharmacology.

The dose of the active compounds can vary depending on factors such as the route of administration, age and weight of patient, nature and severity of the disease to be treated and similar factors. Therefore, any reference herein to a pharmacologically effective amount of the compounds of general formula (I) refers to the aforementioned factors. A proposed dose of the active compounds of this invention, for either oral, parenteral, nasal or buccal administration to an average adult human for the treatment of the conditions referred to above, is 0.1 to 200 mg of the active ingredient per unit dose which could be administered, for example, 1 to 4 times per day.

For illustrative purposes, the reaction scheme depicted herein provides potential routes for synthesizing the compounds of the present invention as well as key intermediates. For a more detailed description of the individual reaction steps, see the Examples section. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in the light of this disclosure using conventional chemistry well known to those skilled in the art.

Commercial reagents were utilized without further purification. Room temperature refers to 25-30° C. IR spectra were taken using KBr and in solid state. Unless otherwise stated, all mass spectra were carried out using ESI conditions. $^1$H-NMR spectra were recorded at 400 MHz on a Bruker instrument. Deuterated chloroform (99.8% D) was used as solvent. TMS was used as internal reference standard. Chemical shift values are expressed in parts per million (δ) values. The following abbreviations are used for the multiplicity for the NMR signals: s=singlet, bs=broad singlet, d=doublet, t=triplet, q=quartet, qui=quintet, h=heptet, dd=double doublet, dt=double triplet, tt=triplet of triplets, m=multiplet. Chromatography refers to column chromatography performed using 100-200 mesh silica gel and executed under nitrogen pressure (flash chromatography) conditions.

The novel compounds of the present invention were prepared according to the procedures of the following schemes and examples, using appropriate materials and are further exemplified by the following specific processes. The most preferred compounds of the invention are any or all of those specifically set forth in these examples. These compounds are not, however, to be construed as forming the only genus that is considered as the invention and any combination of the compounds or their moieties may itself form a genus. The following examples further illustrate details for the preparation of the compounds of the present invention. Those skilled in the art will readily understand that known variations of the conditions and process of the following preparative procedures can be used to prepare these compounds.

Example 1

Preparation of 5-(4-Methylpiperazin-1-yl methyl)-1H-indole

Step (i): Preparation of (3-Methyl-4-nitrophenyl)-(4-methylpiperazin-1-yl)methanone 3-Methyl-4-nitrobenzoic acid (5.525 mmol, 1.0 gram) was taken in a 25 mL two necked round bottom flask attached with a condenser, provided with a guard tube. To this, thionyl chloride (6.07 mmol, 0.735 gram) and 1,2-dichloroethane (5 mL) were added and the solution was refluxed for a period of 3 hours. This reaction mixture was added to another 100 mL flask, containing a solution of N-methylpiperazine (16.57 mmol, 1.66 grams) in 10 mL 1,2-dichloroethane, which is maintained at temperature below 5° C. The reaction mixture was then stirred for 0.5 hour at 25° C. After the completion of reaction, the reaction mixture was poured onto 50 mL water. 1,2-dichloroethane layer was separated, washed with water (2×10 mL), brine (10 mL) and dried over anhydrous sodium sulfate. The volatiles were removed under the reduced pressure to obtain thick syrupy mass. This thick syrupy mass was used for next step of reaction without purification.

Step (ii): Preparation of (4-Methylpiperazin-1-yl)-[4-nitro-3-[2-(pyrrolidin-1-yl)-vinyl]phenyl]methanone (3-Methyl-4-nitrophenyl)-(4-methylpiperazin-1-yl) methanone (3.8022 mmol, 1.0 grams) (obtained from, step (i)) was taken in a 25 mL two necked round bottomed flask attached with a condenser, under nitrogen atmosphere. To this, was added 3 mL of N,N-dimethylformamide, N,N-dimethylformamide dimethylacetal (5.7033 mmol) and pyrrolidine (5.7033 mmol) and refluxed for a period of 6 hours. After the completion of reaction, the reaction mixture was poured on to 20 grams of ice water, basified with 20% NaOH solution (pH to 10) and the mixture was extracted with ethyl acetate (2×30 mL). The combined ethyl acetate extracts were then washed with water (2×30 mL), brine (30 mL) and dried over anhydrous sodium sulfate. The volatiles were removed under reduced pressure to obtain thick syrupy mass. This thick syrupy mass was used for the next step of the reaction without purification.

Step (iii): Preparation of (1H-Indol-5-yl)-(4-methy piperazin-1-yl)methanone (4-Methylpiperazin-1-yl)-[4-nitro-3-(2-pyrrolidin-1-yl-vinyl)phenyl]methanone (2.907 mmol, 1.0 gram) (obtained from step (ii)) was taken in a 25 mL, two necked round bottom flask provided with a condenser, under nitrogen atmosphere. To this THF (7 mL) was added, followed by Raney-Nickel (Ra-Ni) (0.1 gram). Hydrazine hydrate (14.54 mmol, 0.73 gram) was added to the above reaction mixture in such a way that the reaction mixture starts refluxing. The reaction mixture was further refluxed for 3 hours. After the completion of reaction, Ra-Ni was removed by filtration, THF and methanol were distilled off and the concentrate was diluted with water (20 mL), basified with 20% sodium hydroxide solution to pH: 10 and the mixture was extracted with ethyl acetate (2×30 mL). The combined ethyl acetate extracts were then washed with water (2×30 mL), brine (30 Ml) and dried over anhydrous sodium sulfate. The volatiles were removed under the reduced pressure to obtain thick syrupy mass. This thick syrupy mass was purified over silica gel column, eluent being ethyl acetate and triethylamine (0.2 to 1.0%).

Step (iv): Preparation of 5-(4-Methylpiperazin-1-yl methyl)-1H-indole

Lithium aluminium hydride (2.4691 mmol, 0.0938 gram) was taken in a 25 mL two necked round bottom flask provided with a condenser, under nitrogen atmosphere. To this (1H-Indol-5-yl)-(4-methylpiperazin-1-yl)methanone (2.0576 mmol, 0.5 grams) (obtained from step (iii)) dissolved in 5 mL of THF was added and refluxed the mass for a period of 2 hours. After the completion of reaction, the reaction mixture was cooled to 25° C. and quenched by addition of ice-cold water slowly, to decompose the excess of LAH. The resultant precipitate of aluminium hydroxide was removed by filtration over hy-flow. THF was distilled off from this emulsion and the concentrate was diluted with water (20 mL), basified with 20% sodium hydroxide solution to pH: 10 and the mixture was extracted with ethyl acetate (2×20 mL). The combined ethyl acetate extracts were then washed with water (2×20 mL), brine 20 mL and dried over anhydrous sodium sulfate. The volatiles were removed under reduced pressure to obtain thick syrupy mass. This syrupy compound was purified over silica gel column, eluent being ethyl acetate and triethylamine (0.2 to 1.0%).

Example 2

Preparation of 1-Benzenesulfonyl-5-(4-methylpiperazin-1-yl methyl)-1H-indole dihydrochloride 5-(4-Methylpiperazine-1-ylmethyl)-1H-indole (0.8733 mmol, 0.2 gram) (obtained from Example 1) was dissolved in 2 mL N,N-dimethyl formamide. The above solution was then added slowly to 25 mL flask, containing a suspension of sodium hydride (1.31 mmol, 31.4 mg) in 1 mL DMF under nitrogen atmosphere, while maintaining the temperature below 10° C. The reaction mixture was then stirred for a period of 1 hour at 25° C. To this well stirred solution, benzenesulfonyl chloride (1.31 mmol, 0.2312 gram) was added slowly while maintaining the temperature below 10° C. The reaction mixture was further stirred for a period of 2 hours. After the completion of the reaction, the reaction mixture was poured onto 20 grams of ice-water mixture under stirring and the resulting mixture was extracted with ethyl acetate (2×20 mL). The combined ethyl acetate extracts were then washed with water (20 mL), brine (20 mL) and dried over anhydrous sodium sulfate. The volatiles were removed under the reduced pressure to obtain thick syrupy mass, which was purified over silica gel column, eluent being ethyl acetate and triethylamine (0.2 to 1.0%). This material was converted to dihydrochloride salt in diethylether solvent.

Melting Range: 266-270.5° C.
IR spectra (cm$^{-1}$): 3474, 2920, 2417, 1632, 1370, 1182;
Mass (m/z): 370.4 (M+H)$^+$;
$^1$H-NMR (ppm): 2.94 (3H, s), 3.35-3.48 (8H, bs), 4.36 (2H, s), 6.79-6.80 (1H, d, J=3.74 Hz), 7.47-7.52 (3H, m), 7.54-7.62 (1H, m), 7.75 (1H, s), 7.78-7.79 (1H, d, J=3.67 Hz), 7.95-7.97 (2H, m), 8.07-8.09 (1H, d, J=8.6 Hz).

Example 3

The following compounds (2-34) were prepared by following the procedure as described in Example 2, with some non-critical variations.

| | |
|---|---|
| 2. 1-(4-Methylbenzenesulfonyl)-5-(4-methylpiperazin-1-yl methyl)-1H-indole | IR spectra (cm⁻¹): 2962, 2796, 1596, 1371, 1173; Mass (m/z): 384.2 (M + H)⁺; ¹H-NMR (ppm): 2.27 (3H, s), 2.33 (3H, s), 2.43-2.49 (8H, bs), 3.54 (2H, s), 6.60 (1H, d, J = 3.43), 7.20-7.22 (2H, d, J = 8.33), 7.25-7.28 (1H, dd, J = 8.1, 1.49 Hz), 7.45 (1H, d, J = 0.68 Hz), 7.53 (1H, d, J = 3.64), 7.74-7.77 (2H, dd, J = 8.37, 1.58), 7.89-7.91 (1H, d, J = 8.44). |
| 3. 1-(4-Fluorobenzenesulfonyl)-5-(4-methylpiperazin-1-yl methyl)-1H-indole | IR spectra (cm⁻¹): 3131, 2966, 2794, 1586, 1376, 1183; Mass (m/z): 388.2 (M + H)⁺; ¹H-NMR (ppm): 2.27 (3H, s), 2.44-2.45 (8H, bs), 3.55 (2H, s), 6.62-6.63 (1H, d, J = 3.44), 7.08-7.12 (2H, m), 7.27-7.30 (1H, dd, J = 8.48, 1.38 Hz), 7.47 (1H, d, J = 0.70 Hz), 7.51-7.52 (1H, d, J = 3.68), 7.88-7.91 (3H, m). |
| 4. 1-(4-Methoxybenzenesulfonyl)-5-(4-methylpiperazin-1-yl methyl)-1H-indole | IR spectra (cm⁻¹): 3102, 2961, 2798, 1595, 1368, 1141; Mass (m/z): 400.2 (M + H)⁺; ¹H-NMR (ppm): 2.27 (3H, s), 2.44-2.45 (8H, bs), 3.55 (2H, s), 3.79 (3H, s), 6.59-6.60 (1H, d, J = 3.59), 6.87-6.90 (2H, d, J = 9.02), 7.26-7.28 (1H, dd, J = 8.46, 1.48 Hz), 7.45 (1H, s), 7.52-7.53 (1H, d, J = 3.66), 7.81-7.84 (2H, d, J = 8.96), 7.89-7.91 (1H, d, J = 8.50). |
| 5. 1-[4-(1-Methylethyl)benzenesulfonyl]-5-(4-methylpiperazin-1-yl methyl)-1H-indole | IR spectra (cm⁻¹): 2963, 2936, 2794, 1596, 1372, 1174; Mass (m/z): 412.5 (M + H)⁺; ¹H-NMR (ppm): 1.18-1.19 (6H, d, J = 6.84 Hz), 2.27 (3H, s), 2.43-2.45 (8H, m), 2.38-2.48 (1H, m), 3.55 (2H, s), 6.60-6.609 (1H, d, J = 3.48), 7.26-7.29 (3H, m), 7.46 (1H, s), 7.54-7.55 (1H, d, J = 3.68 Hz), 7.78-7.81 (2H, m), 7.91-7.94 (1H, d, J = 8.52). |
| 6. 1-(4-Chlorobenzenesulfonyl)-5-(4-ethylpiperazin-1-yl methyl)-1H-indole dihydrochloride | Melting Range: 265-269° C. IR spectra (cm⁻¹): 3445, 2979, 2333, 1584, 1371, 1183; Mass (m/z): 418.5, 420.5 (M + H)⁺; ¹H-NMR (ppm): 1.15-1.28 (3H, t), 3.02-3.26 (8H, bs), 3.44 (2H, q), 4.39 (2H, s), 6.90-6.91 (1H, d, J = 3.24 Hz), 7.56 (1H, s), 7.67-7.69 (2H, d, J = 8.56 Hz), 7.89-7.90 (1H, d, J = 3.0 Hz), 7.96-7.98 (2H, d, J = 8.36 Hz), 8.03-8.05 (2H, d, J = 8.48 Hz), 11.56 (2H, bs). |
| 7. 1-(4-Fluorobenzenesulfonyl)-5-(4-ethylpiperazin-1-yl methyl)-1H-indole dihydrochloride | Melting Range: 265-270° C. IR spectra (cm⁻¹): 3444, 2983; 2427, 1588, 1377, 1181; Mass (m/z): 402.3 (M + H)⁺; ¹H-NMR (ppm): 1.18-1.22 (3H, t, J = 7.28), 3.16-3.21 (2H, q, J = 7.28 Hz), 3.45 (8H, bs), 4.36 (2H, s), 6.76-6.77 (1H, d, J = 3.64 Hz), 7.10-7.40 (2H, m), 7.32-7.34 (1H, dd, J = 8.56 Hz), 7.63 (1H, s), 7.68-7.69 (1H, d, J = 3.68 Hz), 7.88-7.95 (3H, m). |
| 8. 1-[4-{1-Methylethyl)benzenesulfonyl]-5-(4-ethylpiperazin-1-yl methyl)-1H-indole dihydrochloride | Melting Range: 258-261° C. IR spectra (cm⁻¹): 3421, 2962, 2429, 1594, 1370, 1174; Mass (m/z): 426.4 (M + H)⁺; ¹H-NMR (ppm): 0.90-0.91 (6H, d, J = 6.91 Hz), 1.18-1.22 (3H, t, J = 7.32 Hz), 2.64-2.71 (1H, m), 3.15-3.20 (2H, q, J = 7.3 Hz), 3.24-3.43 (8H, bs), 4.34 (2H, s), 6.73-6.74 (1H, d, J = 3.67 Hz), 7.13-7.15 (2H, d, J = 8.46 Hz), 7.31-7.33 (1H, dd, J = 8.54, 1.35 Hz), 7.60 (1H, s), 7.65-7.69 (3H, d, J = 8.52), 7.92-7.94 (1H, d, J = 8.55 Hz). |
| 9. 1-(4-Methoxybenzenesulfonyl)-5-(4-ethylpiperazin-1-yl methyl)-1H-indole dihydrochloride | Melting Range: 254-258° C. IR spectra (cm⁻¹): 3419, 2982, 2423, 1593, 1371, 1166; Mass (m/z): 414.4 (M + H)⁺; ¹H-NMR (ppm): 1.18-124 (3H, t, J = 7.28 Hz), 3.17-3.22 (2H, q, J = 7.28 Hz), 3.51 (11H, bs), 4.39 (2H, s), 6.55-6.58 (2H, m), 6.70-6.71 (1H, d, J = 3.68), 7.32-7.35 (1H, dd, J = 8.52, 0.9 Hz), 7.54-7.56 (3H, m), 7.61 (1H, s), 7.86-7.88 (1H, d, J = 8.6). |
| 10. 1-(2,4-Difluorobenzenesulfonyl)-5-(4-ethylpiperazin-1-yl methyl)-1H-indole dihydrochloride | Melting Range: 271-274.5° C. IR spectra (cm⁻¹): 3444, 2978, 2344, 1605, 1378, 1181; Mass (m/z): 420.5 (M + H)⁺; ¹H-NMR (ppm): 1.18-1.22 (3H, t, J = 7.33 Hz), 3.15-3.21 (2H, q, J = 7.32 Hz), 3.43 (8H, bs), 4.35 (2H, s), 6.76-6.77 (2H, d, J = 3.74 Hz), 6.96-6.97 (1H, m), 7.06 (1H, m), 7.28-7.31 (1H, dd, J = 8.61, 1.61 Hz), 7.66 (1H, d, J = 1.19 Hz), 7.70-7.71 (1H, m), 7.80-7.81 (1H, d, J = 8.56 Hz), 8.10-8.11 (1H, m). |
| 11. 1-(4-Bromobenzenesulfonyl)-5-(4-ethylpiperazin-1-yl methyl)-1H-indole dihydrochloride | Melting Range: 264.5-267° C. IR spectra (cm⁻¹): 3427, 2977, 2344, 1573, 1371, 1131; Mass (m/z): 462.4, 464.4 (M + H)⁺; ¹H-NMR (ppm): 1.19-1.23 (3H, t, J = 7.30), 3.16-3.21 (2H, q, J = 7.33 Hz), 3.43 (8H, bs), 4.35 (2H, s), 6.77-6.78 (1H, d, J = 3.68 Hz), 7.33-7.35 (1H, dd, J = 8.58, 1.5 Hz), 7.51-7.53 (2H, d, J = 8.67 Hz), 7.63 (1H, s), 7.67-7.70 (3H, m), 7.92-7.94 (1H, d, J = 8.5 Hz). |
| 12. 1-(3-Trifluoromethylbenzenesulfonyl)-5-(4-ethylpiperazin-1-yl methyl)-1H-indole dihydrochloride | Melting Range: 265-270° C. IR spectra (cm⁻¹): 3445, 2978, 2432, 1610, 1376, 1182; Mass (m/z): 452.4 (M + H)⁺; ¹H-NMR (ppm): 1.19-1.23 (3H, t, J = 7.31), 3.16-3.22 (2H, q, J = 7.30 Hz), 3.43 (8H, bs), 4.36 (2H, s), 6.77-6.78 (1H, d, J = 3.68 Hz), 7.33-7.36 (1H, dd, J = 8.50, 0.9 Hz), 7.56-7.63 (2H, m), 7.70-7.71 (1H, d, J = 3.72 Hz), 7.83-7.85 (1H, d, J = 7.88 Hz), |

| | | |
|---|---|---|
| | | 7.96-7.98 (1H, d, J = 8.57 Hz), 8.06-8.08 (1H, d, 8.06 Hz), 8.20 (1H, s). |
| 13. | 1-(4-Methylbenzenesulfonyl)-5-(4-ethylpiperazin-1-yl methyl)-1H-indole dihydrochloride | Melting Range: 263-267° C.<br>IR spectra (cm$^{-1}$): 3447, 2983, 2435, 1630, 1372, 1175;<br>Mass (m/z): 398.4 (M + H)$^+$;<br>$^1$H-NMR (ppm): 1.18-1.23 (3H, t, J = 7.29), 2.16 (3H, s), 3.15-3.21 (2H, q, J = 7.30 Hz), 3.44 (8H, bs), 4.35 (2H, s), 6.74-6.75 (1H, d, J = 3.68 Hz), 7.16-7.18 (2H, d, J = 8.33 Hz), 7.30-7.33 (1H, dd, J = 8.57, 1.62 Hz), 7.62 (1H, d, J = 1.22 Hz), 7.67-7.70 (3H, m), 7.91-7.93 (1H, d, J = 8.54 Hz). |
| 14. | 1-(2,3-Dichlorobenzenesulfonyl)-5-(4-ethylpiperazin-1-yl methyl)-1H-indole dihydrochloride | Melting Range: 273.5-277° C.<br>IR spectra (cm$^{-1}$): 3444, 2984, 2437, 1626, 1377, 1179;<br>Mass (m/z): 452.4, 454.4 (M + H)$^+$;<br>$^1$H-NMR (ppm): 1.18-1.22 (3H, t, J = 7.33 Hz), 3.15-3.21 (2H, q, J = 7.29 Hz), 3.44 (8H, bs), 4.35 (2H, s), 6.75-6.76 (1H, d, J = 3.71 Hz), 7.22-7.25 (1H, dd, J = 1.08, 8.56 Hz), 7.42-7.44 (1H, dt, J = 8.15 Hz), 7.60-7.62 (1H, d, J = 8.58 Hz), 7.67 (1H, s), 7.70-7.72 (1H, dd, J = 0.76, 8.04 Hz), 7.79-7.80 (1H, d, 3.76 Hz), 8.10-8.13 (1H, dd, J = 1.0, 7.99 Hz). |
| 15. | 1-(2-Bromobenzenesulfonyl)-5-(4-ethylpiperazin-1-yl methyl)-1H-indole dihydrochloride | Melting Range: 255.5-259° C.<br>IR spectra (cm$^{-1}$): 3422, 2984, 2437, 1628, 1374, 1179;<br>Mass (m/z): 462.3, 464.3 (M + H)$^+$;<br>$^1$H-NMR (ppm): 1.18-1.22 (3H, t, J = 7.34 Hz), 3.15-3.20 (2H, q, J = 7.35 Hz), 3.44 (8H, bs), 4.35 (2H, s), 6.75-6.76 (1H, d, J = 3.64 Hz), 7.23 (1H, d, J = 1.64 Hz), 7.44 (1H, d, J = 1.69 Hz), 7.50-7.51 (1H, d, J = 1.18 Hz), 7.58-7.60 (1H, d, J = 8.6 Hz), 7.64-7.65 (1H, dd, J = 1.19 Hz), 7.68 (1H, d, J = 1.28 Hz), 7.84-7.85 (1H, d, 3.80 Hz), 8.164-8.168 (1H, dd, J = 7.93, 1.68 Hz). |
| 16. | 1-(4-Chlorobenzenesulfonyl)-5-(4-ethylpipreazin-1-yl methyl)-3-bromo-1H-indole dihydrochloride | Melting Range: 231-235° C.<br>IR spectra (cm$^{-1}$): 3411, 2977, 2442, 1620, 1381, 1183;<br>Mass (m/z): 496.2, 498.2 (M + H)$^+$;<br>$^1$H-NMR (ppm): 1.34-1.38 (3H, t, J = 7.24 Hz), 3.34-3.35 (2H, q), 3.45-3.48 (8H, bs), 4.52 (2H, s), 7.55-7.59 (2H, d, J = 8.73 Hz), 7.64-7.67 (1H, dd, J = 1.5, 8.50 Hz), 7.78 (1H, s), 8.00-8.02 (3H, m), 8.12-8.14 (1H, d, J = 8.56 Hz). |
| 17. | 1-Benzenesulfonyl-5-(4-Ethylpiperazin-1-yl methyl)-1H-indole dihydrochloride | Melting Range: 266-270.5° C.<br>IR spectra (cm$^{-1}$): 3429, 2982, 2424, 1582, 1374, 1176;<br>Mass (m/z): 384.3 (M + H)$^+$;<br>$^1$H-NMR (ppm): 1.13-1.21 (3H, t, J = 7.1 Hz), 3.11-3.47 (10H, m), 3.56 (2H, s), 6.88-6.89 (1H, d, J = 3.5 Hz), 7.51 (1H, s), 7.58-7.62 (2H, m), 7.68-7.70 (1H, m), 7.72 (1H, s), 7.89-7.90 (1H, d, J = 3.47 Hz), 7.97-7.99 (1H, d, J = 8.48 Hz), 8.02-8.03 (2H, m). |
| 18. | 1-(2,4-Difluorobenzenesulfonyl)-5-(4-methylpiperazin-1-yl methyl)-1H-Indole | IR spectra (cm$^{-1}$): 3105, 2930, 2794, 1602, 1379, 1181:<br>Mass (m/z): 406 (M + H)$^+$;<br>$^1$H-NMR (ppm): 2.37 (3H, s), 2.57 (8H, bs), 3.59 (2H, s), 6.64 (1H, d, J = 3.37), 6.82-6.88 (1H, m), 7.01 (1H, m), 7.22-7.25 (1H, dd, J = 8.52, 1.48 Hz), 7.49 (1H, s), 7.60-7.61 (1H, dd, J = 3.25, 3.6 Hz), 7.73-7.75 (1H, d, J = 8.52 Hz), 8.08-8.12 (1H, m). |
| 19. | 1-(2-Chloro-5-trifluoromethylbenzenesulfonyl)-5-(4-methylpiperazin-1-yl methyl)-1H-indole | IR spectra (cm$^{-1}$): 2935, 2808, 1606, 1324, 1144;<br>Mass (m/z): 472.3, 474.3 (M + H)$^+$;<br>$^1$H-NMR (ppm): 2.37 (3H, s), 2.40 (8H, bs), 3.58 (2H, s), 6.65 (1H, d, J = 3.36), 7.22-7.25 (1H, dd, J = 8.56, 1.48 Hz), 7.51 (1H, s), 7.51-7.52 (1H, d, J = 3.84 Hz), 7.57-7.59 (1H, d, J = 8.48 Hz), 7.70-7.71 (1H, dd, J = 3.68 Hz), 7.74-7.76 (1H, dd, J = 8.32, 1.8 Hz), 8.46 (1H, d, J = 1.8 Hz). |
| 20. | 1-(2-Bromobenzenesulfonyl)-5-(4-methylpiperazin-1-yl methyl)-1H-indole | IR spectra (cm$^{-1}$): 3429, 2931, 2805, 2786, 1572, 1369, 1174;<br>Mass (m/z): 448.3, 450.3 (M + H)$^+$;<br>$^1$H-NMR (ppm): 2.28 (3H, s), 2.44 (8H, bs), 3.55 (2H, s), 6.62-6.63 (1H, d, J = 3.76 Hz), 7.20-7.21 (1H, dd, J = 1.4 Hz), 7.40-(1H, dt, J = 1.64 Hz), 7.47-7.48 (1H, dt, J = 1.0 Hz), 7.51 (1H, s), 7.57-7.59 (1H, d, J = 8.52 Hz), 7.66-7.68 (1H, dd, J = 7.88, 1.16 Hz), 7.75-7.76 (1H, d, J = 3.76 Hz), 8.09-8.11 (1H, dd, J = 7.92, 1.8 Hz). |
| 21. | 1-(2,3-Dichlorobenzenesulfonyl)-5-(4-methylpiperazin-1-yl methyl)-1H-indole | IR spectra (cm$^{-1}$): 3391, 2933, 2800, 1459, 1375, 1177;<br>Mass (m/z): 438, 440, 442 (M + H)$^+$;<br>$^1$H-NMR (ppm): 2.33 (3H, s), 2.53 (8H, bs), 3.57 (2H, s), 6.64-6.65 (1H, d, J = 4.04), 7.214 (1H, dd, J = 1.4 Hz), 7.37-7.41 (1H, d, J = 8.08 Hz), 7.51 (1H, s), 7.56-7.58 (1H, d, J = 8.44 Hz), 7.66-7.67 (1H, dd, J = 8.16, 1.4 Hz), 7.68-7.69 (1H, d, J = 3.68 Hz), 8.06-8.08 (1H, dd, J = 8.12, 1.6 Hz). |
| 22. | 1-(4-Chlorobenzenesulfonyl)-5-(4-methylpiperazin-1-yl methyl)-1H-indole | IR spectra (cm$^{-1}$): 3123, 2928, 2796, 1582, 1376, 1172;<br>Mass (m/z): 404, 406 (M + H)$^+$;<br>$^1$H-NMR (ppm): 2.24 (3H, s), 2.4 (8H, bs), 3.56 (2H, s), 6.63-6.65 (1H, d, J = 0.6 Hz), 7.27-7.30 (1H, dd, J = 8.52, 1.4 Hz), 7.39-7.41 (2H, d, J = 7.04 Hz), 7.47 (1H, s), 7.50-7.51 (1H, d, J = 3.64 Hz), 7.80-7.82 (2H, d, J = 8.72 Hz), 7.88-7.90 (1H, d, J = 8.44 Hz). |

| | |
|---|---|
| 23. 1-(3-Trifluoromethylbenzenesulfonyl)-5-(4-methylpiperazin-1-yl-methyl)-1H-indole dihydrochloride | IR spectra (cm$^{-1}$): 3435, 2979, 2510, 1609, 1374, 1182; Mass (m/z): 438 (M + H)$^+$; $^1$H-NMR (ppm): 2.76 (3H, s), 3.35 (8H, bs), 4.38 (2H, s), 6.93 (1H, d, J = 3.48 Hz), 7.59 (1H, bs), 7.83-7.87 (2H, m), 8.01-8.06 (2H, m), 8.10-8.12 (1H, m), 8.36-8.41 (2H, m), 11.8 (2H, bs). |
| 24. 1-(4-Chlorobenzenesulfonyl)-3-chloro-5-(4-methylpiperazin-1-yl methyl)-1H-indole | Melting Range: 139.2-140.4° C. IR spectra (cm$^{-1}$): 3145, 2938, 2796, 1579, 1382, 1183; Mass (m/z): 438.3, 440.3 (M + H)$^+$; $^1$H-NMR (ppm): 2.37 (3H, s), 2.42 (8H, bs), 3.60 (2H, s), 7.35-7.37 (1H, dd, J = 8.6, 1.49 Hz), 7.41-7.44 (2H, d, J = 8.72 Hz), 7.48 (1H, d, J = 0.66 Hz), 7.51 (1H, s), 7.80-7.82 (2H, d, J = 8.72 Hz), 7.89-7.91 (1H, d, J = 8.56 Hz). |
| 25. 1-(4-Fluorobenzenesulfonyl)-3-chloro-5-(4-methylpiperazin-1-yl methyl)-1H-indole | Melting Range: 118.8-120.1° C. IR spectra (cm$^{-1}$): 3145, 2942, 2833, 1587, 1379, 1182; Mass (m/z): 422.3, 424.3 (M + H)$^+$; $^1$H-NMR (ppm): 2.39 (3H, s), 2.44 (8H, bs), 3.61 (2H, s), 7.11-7.15 (2H, m), 7.34-7.37 (1H, dd, J = 8.51, 1.34 Hz), 7.48 (1H, s), 7.52 (1H, s), 7.89-7.92 (3H, m). |
| 26. 1-(2,4-Difluorobenzenesulfonyl)-3-chloro-5-(4-methylpiperazin-1-yl methyl)-1H-indole dihydrochloride | Melting Range: 251.85-253° C. IR spectra (cm$^{-1}$): 3437, 3150, 2985, 2346, 1600, 1383, 1182; Mass (m/z): 440.4, 442 (M + H)$^+$; $^1$H-NMR (ppm): 2.85 (3H, s), 3.42 (8H, bs), 4.36 (2H, s), 6.93-6.94 (1H, m), 6.95-6.98 (1H, m), 7.34-7.37 (1H, dd, J = 8.64, 1.48 Hz), 7.62 (1H, d, J = 1.024 Hz), 7.75-7.76 (1H, d, J = 1.92 Hz), 7.79-7.82 (1H, d, J = 8.6 Hz), 8.05-8.08 (1H, m). |
| 27. 1-(2-Chloro-5-trifluoromethylbenznesulfonyl)-3-chloro-5-(4-methylpiperazin-1-yl methyl)-1H-indole dihydrochloride | Melting Range: 287-290° C. IR spectra (cm$^{-1}$): 3435, 3166, 2979, 2311, 1604, 1372, 1177; Mass (m/z): 506.3, 508.3 (M + H)$^+$; $^1$H-NMR (ppm): 2.84 (3H, s), 3.37 (8H, bs), 4.32 (2H, s), 7.31-7.33 (1H, dd, J = 8.6, 1.59 Hz), 7.62-7.60 (1H, d, J = 8.35 Hz), 7.65 (1H, d, J = 1.18 Hz), 7.67-7.69 (1H, d, J = 8.62 Hz), 7.84-7.87 (1H, dd, J = 8.37, 1.74 Hz), 7.91 (1H, s), 8.56 (1H, d, J = 1.72 Hz). |
| 28. 1-(4-Fluorobenznesulfonyl)-4-isopropoxy-5-(4-methylpiperazin-1-yl methyl)-1H-indole | IR spectra (cm$^{-1}$): 3105, 2935, 2796, 1591, 1458, 1376, 1185; Mass (m/z): 446.3 (M + H)$^+$; $^1$H-NMR (ppm): 1.29-1.30 (6H, d), 2.26 (3H, s), 2.3-2.6 (8H, bs), 3.6 (2H, s), 4.44-4.50 (1H, m), 6.69-6.7 (1H, d, J = 3.72 Hz), 7.1-7.14 (2H, m), 7.34-7.36 (1H, d, J = 8.5 Hz), 7.45-7.46 (1H, d, J = 3.672 Hz), 7.62-7.64 (1H, d, J = 8.46 Hz), 7.88-7.92 (2H, m). |
| 29. 1-[4-(1-Methylethyl)benzenesulfonyl]-4-isopropoxy-5-(4-methylpiperazin-1-yl methyl)-1H-indole | IR spectra (cm$^{-1}$): 2966, 1596, 1458, 1372, 1182; Mass (m/z): 470.4 (M + H)$^+$; $^1$H-NMR (ppm): 1.19-1.21 (6H, d), 1.29-1.31 (6H, d), 2.27 (3H, s), 2.34-2.6 (8H, bs), 2.9 (1H, m), 3.6 (2H, s), 4.47-4.5 (1H, m), 6.67-6.68 (1H, d, J = 4.08 Hz), 7.27-7.29 (2H, m), 7.32-7.34 (1H, d, J = 8.52 Hz), 7.47-7.48 (1H, d, J = 3.68 Hz), 7.65-7.67 (1H, d, J = 8.32 Hz), 7.78-7.8 (2H, m). |
| 30. 1-(4-Fluorobenzenesulfonyl)-3-chloro-5-(piperazin-1-yl methyl)-1H-indole dihydrochloride | Melting Range: 254-259.6° C. IR spectra (cm$^{-1}$): 3425, 1585, 1381, 1273, 1180, 840, 574; Mass (m/z): 408.3 (M + H)$^+$; $^1$H-NMR (ppm): 3.35 (8H, bs), 4.32 (2H, s), 7.46-7.50 (2H, m), 7.73-7.75 (1H, d, J = 8.34 Hz), 7.92 (1H, s), 8.05-8.07 (1H, d, J = 8.59 Hz), 8.18-8.21 (2H, m), 8.25 (1H, s), 9.71 (2H, s), 12.05 (1H, bs). |
| 31. 1-(2-Bromobenzenesulfonyl)-5-(piperazin-1-yl methyl)-1H-indole dihydrochloride | Melting Range: 264.2-266.9° C. IR spectra (cm$^{-1}$): 3415, 1373, 1274, 1178, 588; Mass (m/z): 434.3, 436.3 (M + H)$^+$; $^1$H-NMR (ppm): 3.32 (8H, bs), 4.27 (2H, s), 6.64-6.65 (1H, d, J = 3.75 Hz), 7.11-7.13 (1H, dd, J = 8.57, 1.62 Hz), 7.29-7.33 (1H, dt, J = 7.76, 1.65 Hz), 7.37-7.41 (1H, dt, J = 7.63, 1.22 Hz), 7.47-7.53 (2H, m), 7.57-7.58 (1H, d, J = 1.21 Hz), 7.72 (1H, d, J = 3.76 Hz), 8.02-8.04 (1H, dd, J = 7.98, 1.6 Hz). |
| 32. 1-(2,4-Difluorobenzenesulfonyl)-3-chloro-5-(piperazin-1-yl methyl)-1H-indole dihydrochloride | Melting Range: 241.5-246.1° C. IR spectra (cm$^{-1}$): 3446, 1600, 1433, 1384, 1274, 1182, 586; Mass (m/z): 426.2, 428.2 (M + H)$^+$; $^1$H-NMR (ppm): 3.38 (8H, bs), 4.34 (2H, s), 6.94-7.07 (2H, m), 7.36-7.38 (1H, d, J = 8.45 Hz), 7.64 (1H, s), 7.79-7.84 (2H, m), 8.05-8.11 (1H, m). |
| 33. 1-(Benzenesulfonyl)-5-(piperazin-1-yl methyl)-1H-indole dihydrochloride | Melting Range: 250.4-256.2° C. IR spectra (cm$^{-1}$): 3421, 1448, 1371, 1274, 1176, 1132, 580; Mass (m/z): 356.4 (M + H)$^+$; $^1$H-NMR (ppm): 3.28 (8H, bs), 4.21 (2H, s), 6.64 (1H, d, J = 4.08 Hz), 7.20-7.23 (1H, dd, J = 8.59, 1.57 Hz), 7.27-7.31 (2H, m), 7.39-7.43 (1H, m), 7.50-7.51 (1H, d, J = 1.05 Hz), 7.61 (1H, d, 3.71 Hz); 7.72-7.74 (2H, m), 7.82-7.84 (1H, d, J = 8.54). |

| | |
|---|---|
| 34. 1-[4-(1-Methylethyl) benzenesulfonyl]-5-(piperazin-1-yl methyl)-1H-indole dihydrochloride | Melting Range: 250-254° C.<br>IR spectra (cm$^{-1}$): 3427, 1462, 1371, 1276, 1170, 1132, 590;<br>Mass (m/z): 398.3 (M + H)$^+$;<br>$^1$H-NMR (ppm): 0.77-0.79 (6H, d, 6.89 Hz); 2.52-2.55 (1H, sept), 3.33 (8H, bs), 4.27 (2H, s), 6.63-6.64 (1H, d, J = 3.66 Hz), 6.97-6.99 (2H, d, J = 8.62 Hz), 7.23-7.25 (1H, d, J = 8.6 Hz), 7.52-7.55 (4H, m), 7.82-7.84 (1H, d, J = 8.56 Hz). |

Example 4

The following compound (35-40) can be prepared by the person skilled in the art by following the procedure described in Example 2.

| | |
|---|---|
| 35. | 1-(3-Chloro benzenesulfonyl)-5-(2,4-dimethyl piperazin-1-ylmethyl)-1H-indole |
| 36. | 2-Chloro-5-(4-methyl piperazin-1-ylmethyl)-1-(3-methyl benzesulfonyl)-1H-indole |
| 37. | 2-Methoxy-5-(4-methyl piperazin-1-ylmethyl)-1-(3-methyl benzenesulfonyl)-1H-indole |
| 38. | 1-(3-Chloro benzenesulfonyl)-3-methoxy-5-(4-methyl piperazin-1-ylmethy)-1H-indole |
| 39. | 5-(4-Methyl piperazin-1-ylmethyl)-1-(4-methyl benzenesulfonyl)-6-trifluoromethyl-1H-indole |
| 40. | 1-(3-Chloro benzenesulfonyl)-7-methoxy-5-(4-methyl piperazin-1-ylmethyl)-1H-indole |

Example 5

Food Intake Measurement (Behavioural Model)

Male Wister rats (120-140 grams) obtained from N. I. N. (National Institute of Nutrition, Hyderabad, India) were used. The chronic effect of the compounds of general formula (I) on food intake in well-fed rats was then determined as follows.

The rats were housed in single home cages for 28 days. During this period, the rats were either dosed orally or ip, with a composition comprising a compound of formula (I) or a corresponding composition (vehicle) without the said compound (control group), once a day. The rat is provided with ad libitum food and water.

On 0, 1$^{st}$, 7$^{th}$, 14$^{th}$, 21$^{st}$ and 28$^{th}$ day the rats were left with the pre-weighed amounts of food. Food intake and weight gain were measured on a routine basis. Also a food ingestion method is disclosed in the literature (Kask et al., European Journal of Pharmacology, 414, 2001, 215-224 and Turnball et. al., Diabetes, vol 51, August, 2002, and some in-house modifications). The respective parts of the descriptions are herein incorporated as a reference and they form part of the disclosure.

Some representative compounds have shown the statistically significant decrease in food intake, when conducted in the above manner at the doses of either 10 mg/Kg or 30 mg/Kg or both.

Example 6

Tablet Comprising a Compound of Formula (I)

| | |
|---|---|
| Compound according to Example 2 | 5 mg |
| Lactose | 60 mg |
| Crystalline cellulose | 25 mg |
| K 90 Povidone | 5 mg |
| Pregelatinised starch | 3 mg |
| Colloidal silicon dioxide | 1 mg |
| Magnesium stearate | 1 mg |
| Total weight per tablet | 100 mg |

The ingredients were combined and granulated using a solvent such as methanol. The formulation was then dried and formed into tablets (containing about 20 mg of active compound) with an appropriate tablet machine.

Example 7

Composition for Oral Administration

| Ingredient | % wt./wt. |
|---|---|
| Active ingredient | 20.0% |
| Lactose | 79.5% |
| Magnesium stearate | 0.5% |

The ingredients were mixed and dispensed into capsules containing about 100 mg each; one capsule would approximate a total daily dosage.

Example 8

Liquid Oral Formulation

| Ingredient | Amount |
|---|---|
| Active ingredient | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 g |
| Colorings | 0.5 g |
| Distilled water | q.s. to 100 mL |

The ingredients were mixed to form a suspension for oral administration.

Example 9

Parenteral Formulation

| Ingredient | % wt./wt. |
|---|---|
| Active ingredient | 0.25 g |
| Sodium Chloride | qs to make isotonic |
| Water for injection to | 100 mL |

The active ingredient was dissolved in a portion of the water for injection. A sufficient quantity of sodium chloride was then added with stirring to make the solution isotonic. The solution was made up to weight with the remainder of the water for injection, filtered through a 0.2 micron membrane filter and packaged under sterile conditions.

Example 10

Suppository Formulation

| Ingredient | % wt./wt. |
|---|---|
| Active ingredient | 1.0% |
| Polyethylene glycol 1000 | 74.5% |
| Polyethylene glycol 4000 | 24.5% |

The ingredients were melted together and mixed on a steam bath and poured into molds containing 2.5 grams total weight.

Example 11

Topical Formulation

| Ingredients | Grams |
|---|---|
| Active ingredient | 0.2-2 g |
| Span 60 | 2 g |
| Tween 60 | 2 g |
| Mineral oil | 5 g |
| Petrolatum | 10 g |
| Methyl paraben | 0.15 g |
| Propyl paraben | 0.05 g |
| BHA (butylated hydroxy anisole) | 0.01 g |
| Water | 100 mL |

All of the ingredients, except water, were combined and heated to about 60° C. with stirring. A sufficient quantity of water at about 60° C. was then added with vigorous stirring to emulsify the ingredients and then water added q.s about 100 grams.

Example 12

Object Recognition Task Model

The cognition-enhancing properties of compounds of this invention were estimated using a model of animal cognition: the object recognition task model.

Male Wister rats (230-280 grams) obtained from N. I. N. National Institute of Nutrition, Hyderabad, India) were used as experimental animals. Four animals were housed in each cage. Animals were kept on 20% food deprivation before one day and given water ad libitum throughout the experiment and maintained on a 12 hours light/dark cycle. Also the rats were habituated to individual arenas for 1 hour in the absence of any objects.

One group of 12 rats received vehicle (1 mL/Kg) orally and another set of animals received compound of the formula (I) either orally or i.p., before one hour of the familiar (T1) and choice trial (T2).

The experiment was carried out in a 50×50×50 cm open field made up of acrylic. In the familiarization phase, (T1), the rats were placed individually in the open field for 3 minutes, in which two identical objects (plastic bottles, 12.5 cm height×5.5 cm diameter) covered in yellow masking tape alone (a1 and a2) were positioned in two adjacent corners, 10 cm. from the walls. After 24 hours of the (T1) trial for long-term memory test, the same rats were placed in the same arena as they were placed in T1 trial. Choice phase (T2) rats were allowed to explore the open field for 3 minutes in presence of one familiar object (a3) and one novel object (b) (Amber color glass bottle, 12 cm high and 5 cm in diameter. Familiar objects presented similar textures, colors and sizes. During the T1 and T2 trial, explorations of each object (defined as sniffing, licking, chewing or having moving vibrissae whilst directing the nose towards the object at a distance of less than 1 cm) were recorded separately by stopwatch. Sitting on an object was not regarded as exploratory activity, however, it was rarely observed.

T1 is the total time spent exploring the familiar objects (a1+a2).

T2 is the total time spent exploring the familiar object and novel object (a3+b).

The object recognition test was performed as described by Ennaceur, A., Delacour, J., 1988, A new one-trial test for neurobiological studies of memory in rats—Behavioral data, Behav. Brain Res., 31, 47-59.

Some representative compounds have shown positive effects indicating the increased novel object recognition viz; increased exploration time with novel object and higher discrimination index.

Example 13

Chewing/Yawning/Stretching Induction by 5-HT$_6$ R Antagonists

Male Wister rats weighing 200-250 grams were used. Rats were given vehicle injections and placed in individual, transparent chambers for 1 hour each day for 2 days before the test day, to habituate them to the observation chambers and testing procedure. On the test day, rats were placed in the observation chambers immediately after drug administration and observed continuously for yawning, stretching and chewing behaviors from 60 to 90 minutes after drug or vehicle injections. 60 minutes prior to the drug administration Physostigmine, 0.1 mg/kg i.p, was administered to all the animals. Average number of yawns, stretches and vacuous chewing movements during the 30 minutes observation period were recorded.

Reference: (A) King M. V., Sleight A., J., Woolley M. L., and et. al., Neuropharmacology, 2004, 47, 195-204. (B) Bentey J. C., Bourson A., Boess F. G., Fone K. C. F., Marsden C. A., Petit N., Sleight A. J., British Journal of Pharmacology, 1999, 126(7), 1537-1542).

Example 14

Water Maze

The water maze apparatus consisted of a circular pool (1.8 m diameter, 0.6 m high) constructed in black Perspex (TSE systems, Germany) filled with water (24±2° C.) and positioned underneath a wide-angled video camera to track animal. The 10 cm$^2$ perspex platform, lying 1 cm below the water surface, was placed in the centre of one of the four imaginary quadrants, which remained constant for all rats. The black Perspex used in the construction of the maze and platform offered no intramaze cues to guide escape behavior. By contrast, the training room offered several strong extramaze visual cues to aid the formation of the spatial map necessary for escape learning. An automated tracking system, [Videomot 2 (5.51), TSE systems, Germany] was employed. This program analyzes video images acquired via a digital camera and an image acquisition board that determined path length, swim speed and the number of entries and duration of swim time spent in each quadrant of the water maze.

Reference: (A) Yamada N., Hattoria A., Hayashi T., Nishikawa T., Fukuda H. et. Al., Pharmacology, Biochem. And Behaviour, 2004, 78, 787-791. (B) Linder M. D., Hodges D. B., Hogan S. B., Corsa J. A., et al The Journal of Pharmacology and Experimental Therapeutics, 2003, 307 (2), 682-691.

Example 15

Passive Avoidance Apparatus

Animals were trained in a single-trial, step through, light-dark passive avoidance paradigm. The training apparatus consisted of a chamber 300 mm in length, 260 mm wide and 270 mm in height, constructed to established designs. The front and top were transparent, allowing the experimenter to observe the behavior of the animal inside the apparatus. The chamber was divided into two compartments, separated by a central shutter that contained a small opening 50 mm wide and 75 mm high set close to the front of the chamber. The smaller of the compartments measured 9 mm in width and contained a low-power (6V) illumination source. The larger compartment measured 210 mm in width and was not illuminated. The floor of this dark compartment consisted of a grid of 16 horizontal stainless-steel bars that were 5 mm in diameter and spaced 12.5 mm apart. A current generator supplied 0.75 mA to the grid floor, which was scrambled once every 0.5 seconds across the 16 bars. A resistance range of 40-60 micro ohms was calculated for a control group of rats and the apparatus was calibrated accordingly. An electronic circuit detecting the resistance of the animal ensured an accurate current delivery by automatic variation of the voltage with change in resistance.

Experimental Procedure:

This was carried out as described previously (Fox et al., 1995). Adult male Wister rats weighing 200-230 grams were used. Animals were brought to the laboratory 1 hour before the experiment. On the day of training, animals were placed facing the rear of the light compartment of the apparatus. The timer was started once the animal has completely turned to face the front of the chamber. Latency to enter the dark chamber was recorded (usually <20 seconds) and having completely entered the dark compartment an inescapable foot shock of 0.75 mA for 3 seconds was administered to the animal, Animals were then returned to their home cages. Between each training session, booth compartments of the chamber were cleaned to remove any confounding olfactory cues. Recall of this inhibitory stimulus was evaluated 24 hours, 72 hours and on 7 day post-training by returning the animal into the light chamber and recording their latency to enter the dark chamber, a criterion time of 300 seconds was employed.

Reference: (A) Callahan P. M., Ilch C. P., Rowe N. B., Tehim A., Abst. 776.19.2004, Society for neuroscience, 2004. (B) Fox G. B., Connell A. W. U., Murphy K. J., Regan C. M., Journal of Neurochemistry, 1995, 65, 6, 2796-2799.

Example 16

Binding Assay for Human 5-HT$_6$ Receptor

Compounds can be tested according to the following the procedures.

Materials and Methods:
  Receptor source: Human recombinant expressed in HEK293 cells
  Radioligand [$^3$H]LSD (60-80 Ci/mmol)
  Final ligand concentration—[1.5 nM]
  Non-specific determinant: Methiothepin mesylate—[0.1 µM]
  Reference compound: Methiothepin mesylate
  Positive control: Methiothepin mesylate
Incubation Conditions:
  Reactions were carried out in 50 µM TRIS-HCl (pH 7.4) containing 10 µM MgCl$_2$, 0.5 mM EDTA for 60 minutes at 37° C. The reaction was terminated by rapid vacuum filtration onto glass fiber filters. Radioactivity trapped onto the filters was determined and compared to control values in order to ascertain any interactions of test compound(s) with the cloned serotonin 5-HT$_6$ binding site.

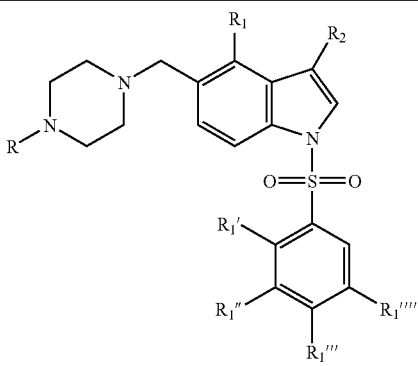

| Ex. No. | Salt/ Base | R | $R_1$ | $R_2$ | $R_1'$ | $R_1''$ | $R_1'''$ | $R_1''''$ | Radio- ligand binding data at 5-HT$_6$ (h) Ki (nM) |
|---|---|---|---|---|---|---|---|---|---|
| 1 | Di-HCl | CH$_3$ | H | H | H | H | H | H | 3.83 |
| 3 | — | CH$_3$ | H | H | H | H | F | H | 14.6 |
| 5 | — | CH$_3$ | H | H | H | H | Pr$^i$ | H | 17.9 |
| 7 | Di-HCl | C$_2$H$_5$ | H | H | H | H | F | H | 3.21 |
| 8 | Di-HCl | C$_2$H$_5$ | H | H | H | H | Pr$^i$ | H | 5.81 |
| 10 | Di-HCl | C$_2$H$_5$ | H | H | F | H | F | H | 12.4 |
| 14 | Di-HCl | C$_2$H$_5$ | H | H | Cl | Cl | H | H | 5.52 |
| 15 | Di-HCl | C$_2$H$_5$ | H | H | Br | H | H | H | 2.56 |

-continued

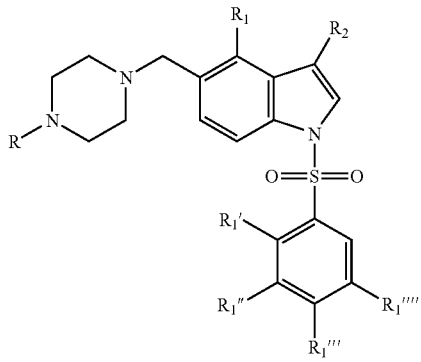

| Ex. No. | Salt/Base | R | $R_1$ | $R_2$ | $R_1'$ | $R_1''$ | $R_1'''$ | $R_1''''$ | Radioligand binding data at 5-$HT_6$(h) Ki (nM) |
|---|---|---|---|---|---|---|---|---|---|
| 19 | — | $CH_3$ | H | H | Cl | H | H | $CF_3$ | 11.3 |
| 20 | — | $CH_3$ | H | H | Br | H | H | H | 8.3 |
| 21 | — | $CH_3$ | H | H | Cl | Cl | H | H | 18 |
| 22 | — | $CH_3$ | H | H | H | H | Cl | H | 3.02 |
| 25 | — | $CH_3$ | H | Cl | H | H | F | H | 2.97 |
| 26 | Di-HCl | $CH_3$ | H | Cl | F | H | F | H | 3.36 |
| 27 | Di-HCl | $CH_3$ | H | Cl | Cl | H | H | $CF_3$ | 4.16 |
| 28 | — | $CH_3$ | $OPr^i$ | H | H | H | F | H | 276 |
| 30 | Di-HCl | H | H | H | Cl | H | F | H | 2.58 |
| 31 | Di-HCl | H | H | H | Br | H | H | H | 7.77 |
| 32 | Di-HCl | H | H | H | Cl | F | H | F | 5.77 |
| 33 | Di-HCl | H | H | H | H | H | H | H | 2.52 |
| 34 | Di-HCl | H | H | H | H | H | $Pr^i$ | H | 14.9 |

Literature Reference: Monsma F. J. Jr., et al., Molecular Cloning and Expression of Novel Serotonin Receptor with High Affinity for Tricyclic Psychotropic Drugs. Mol. Pharmacol. (43): 320-327 (1993).

Example 17

5-$HT_6$ Functional Assay Cyclic AMP

The antagonist property of the compounds at the human 5-$HT_6$ receptors was determined by testing their effect on cAMP accumulation in stably transfected HEK293 cells. Binding of an agonist to the human 5-$HT_6$ receptor will lead to an increase in adenyl cyclase activity. A compound that is an agonist will show an increase in CAMP production and a compound that is an antagonist will block the agonist effect.

Human 5-$HT_6$ receptors were cloned and stably expressed in HEK293 cells. These cells were plated in 6 well plates in DMEM/FI2 media with 10% fetal calf serum (FCS) and 500 μg/mL G418 and incubated at 37° C. in a $CO_2$ incubator. The cells were allowed to grow to about 70% confluence before initiation of the experiment. On the day of the experiment, the culture media was removed and the cells were washed once with serum free medium (SFM). Two mL of SFM+IBMX media was added and incubated at 37° C. for 10 minutes. The media were removed and fresh SFM+IBMX media containing various compounds and 1 μM serotonin (as antagonist) were added to the appropriate wells and incubated for 30 minutes. Following incubation, the media were removed and the cells were washed once with 1 mL of PBS (phosphate buffered saline). Each well was treated with 1 mL cold 95% ethanol and 5 μM EDTA (2:1) at 4° C. for 1 hour. The cells were then scraped and transferred into Eppendorf tubes. The tubes were centrifuged for 5 minutes at 4° C. and the supernatants were stored at 4° C. until assayed.

cAMP content was determined by EIA (enzyme-immunoassay) using the Amersham Biotrak cAMP EIA kit (Amersham RPN 225). The procedure used is as described for the kit. Briefly, cAMP is determined by the competition between unlabeled cAMP and a fixed quantity of peroxidase-labelled cAMP for the binding sites on anti-cAMP antibody. The antibody is immobilized onto polystyrene microtitre wells precoated with a second antibody. The reaction is started by adding 50 uL, peroxidase-labeled cAMP to the sample (100 μl) pre-incubated with the antiserum (100 mL) for 2 hours at 4° C. Following 1 hour incubation at 4° C., the unbound ligand is separated by a simple washing procedure. Then an enzyme substrate, trimethylbenzidine is added and incubated at room temperature for 60 minutes. The reaction is stopped by the addition of 100 mL, 1.0 M sulphuric acid and the resultant color read by a microtitre plate spectrophotometer at 450 nm within 30 minutes.

In the functional adenylyl cyclase assay, some of the compound of this invention was found to be a competitive antagonist with good selectivity over a number of other receptors including other serotonin receptors such as 5-$HT_{1A}$ and 5-$HT_7$.

Example 18

Rodent Pharmacokinetic Study

Male wistar rats (230-280 grams) obtained from N. I. N. (National Institute of Nutrition, Hyderabad, India) were used as an experimental animal.

Three to five animals were housed in each cage. Animals were kept on 20% food deprivation before one day and given water ad libitum throughout the experiment and maintained on a 12 hours light/dark cycle. One group of rats received NCE compound (3-30 mg/Kg) orally and another group of animals received same compound intravenously.

At each time point blood was collected by jugular vein. Plasma was stored frozen at −20° C. until analysis. The concentrations of the NCE compound in plasma were determined using LC-MS/MS method.

Schedule time points: Pre dose 0.25, 0.5, 1, 1.5, 2, 3, 4, 6, 8, 10, 12 and 24 hours after dosing (n=3). The NCE compounds were quantified in plasma by validated LC-MS/MS method using solid phase extraction technique. NCE compounds were quantified in the calibration range of 2-2000 ng/ml in plasma and brain homogenate. Study samples were analyzed using calibration samples in the batch and quality control samples spread across the batch.

Pharmacokinetic parameters Cmax, Tmax, AUCt, AUCinf, half life, volume of distribution, clearance, mean residence time and thereby oral bioavailability were calculated by non-compartmental model using software WinNonlin version 4.1.

Example 19

Rodent Brain Penetration Study

Male Wister rats (230-280 grams) obtained from N. I. N. (National Institute of Nutrition, Hyderabad, India) were used as an experimental animal.

Three to five animals were housed in each cage. Animals were kept on 20% food deprivation before one day and given water ad libitum throughout the experiment, and maintained on a 12 hours light/dark cycle. Each group of animals received NCE compound (3-30 mg/Kg) orally or ip.

At each time point blood was collected by jugular vein. Animals will be sacrificed to collect the brain tissue and was homogenized. Plasma and Brain was stored frozen at −20° C. until analysis. The concentrations of the NCE compound in plasma and Brain were determined using LC-MS/MS method.

Schedule time points: Pre dose 0.25, 0.5, 1, 1.5, 2, 3, 4, 6, 8, 10, 12 and 24 hours after dosing (n=3). The NC compounds were quantified in plasma and brain homogenate by validated LC-MS/MS method using solid phase extraction technique. NCE compounds were quantified in the calibration range of 2-2000 ng/ml in plasma and brain homogenate. Study samples were analyzed using calibration samples in the batch and quality control samples spread across the batch.

Pharmacokinetic parameters Cmax, Tmax, AUCt, AUCinf, half life, volume of distribution, clearance, mean residence time and thereby Cb/Cp, ratio of NCE in brain versus plasma were calculated by non-compartmental model using software WinNonlin version 4.1.

Example 20

Rodent Brain Micro Dialysis Study for Possible Modulation of Neurotransmitters

Male Wister rats (230-280 grams) obtained from N. I. N. (National Institute of Nutrition, Hyderabad, India) were used as an experimental animal.

Group allocation Group 1: Vehicle (Water; 5 mL/kg; p.o.), Group 2: NCE (3 mg/kg; p.o.), Group 3: NCE (10 mg/kg; p.o.)

Surgical Procedure: Rats were anesthetized with chloral hydrate and placed in Stereotaxic frame. Guide cannula (CMA/12) was placed at AP: −5.2 mm, ML: +5.0 mm relative from bregma and DV: −3.8 mm from the brain surface according to the atlas of Paxinos and Watson (1986). While the animal was still anesthetized, a micro dialysis probe (CMA/12, 4 mm, PC) was inserted through the guide cannula and secured in place. After surgery recovery period of 48-72 hours was maintained before subjecting the animal for study.

A day prior to study animals were transferred to home cages for acclimatization and implanted probe was perfused overnight with a modified Ringer's solution comprised of: 1.3 µM CaCl2 (Sigma), 1.0 µM $MgCl_2$ (Sigma), 3.0 µM KCl (Sigma), 147.0 µM NaCl (Sigma), 1.0 µM $Na_2HPO_4.7H_2O$ and 0.2 µM $NaH_2PO_4.2H_2O$ and 0.3 µM neostigmine bromide (Sigma) (pH to 7.2) at a rate of 0.2 µL/minute set by a microinfusion pump (PicoPlus, Harward). On the day of experiment perfusion rate was changed to 1.2 µL/minutes and allowed for 3 hours stabilization. After stabilization period, four basals were collected at 20 minutes intervals before dosing. Dialysate samples were collected in glass vials using CMA/170 refrigerated fraction collector.

Vehicle or NCE (3 mg/kg or 10 mg/kg) was administered by gavage after four fractions had been collected. The perfusate was collected until 6 hours after administration.

Acetylcholine concentrations in dialysate samples were measured by LC-MS/MS (API 4000, MDS SCIEX) method. Acetylcholine is quantified in the calibration range of 0.250 to 8.004 ng/mL in dialysates.

On completion of the microdialysis experiments, the animals were sacrificed and their brains were removed and stored in a 10% formalin solution. Each brain was sliced at 50µ on a cryostat (Leica) stained and examined microscopically to confirm probe placement. Data from animals with incorrect probe placement were discarded.

Microdialysis data were expressed as percent changes (Mean±S.E.M.) of baseline that was defined as the average absolute value (in fM/10 µL) of the four samples before drug administration.

Effects of NCE (3 & 10 mg/kg) and Vehicle treatments were statistically evaluated by one-way ANOVA followed by Dunnett's multiple comparison tests. In all statistical measures, a $p<0.05$ was considered significant. The Graph Pad Prism program statistically evaluated the data.

We claim:
1. A compound which is selected from the group consisting of:
   1-(4-Chlorobenzenesulfonyl)-5-(4-ethylpiperazin-1-yl methyl)-1H-indole dihydrochloride;
   1-(4-Fluorobenzenesulfonyl)-5-(4-ethylpiperazin-1-yl methyl)-1H-indole dihydrochloride;
   1-(4-Bromobenzenesulfonyl)-5-(4-ethylpiperazin-1-yl methyl)-1H-indole dihydrochloride;
   1-(2-Bromobenzenesulfonyl)-5-(4-ethylpiperazin-1-yl methyl)-1H-indole dihydrochloride;
   1-(4-Chlorobenzenesulfonyl)-5-(4-ethylpiperazin-1-yl methyl)-3-bromo-1H-indole dihydrochloride;
   1-(4-Chlorobenzenesulfonyl)-3-chloro-5-(4-methylpiperazin-1-yl methyl)-1H-indole;
   1-(4-Fluorobenzenesulfonyl)-3-chloro-5-(4-methylpiperazin-1-yl methyl)-1H-indole;
   1-(2,4-Difluorobenzenesulfonyl)-3-chloro-5-(4-methylpiperazin-1-yl methyl)-1H-indole dihydrochloride;
   1-(2-Chloro-5-trifluoromethylbenzenesulfonyl)-3-chloro-5-(4-methylpiperazin-1-yl methyl)-1H-indole dihydrochloride;
   1-(4-Fluorobenzenesulfonyl)-4-isopropoxy-5-(4-methylpiperazin-1-yl methyl)-1H-indole;
   1-[4-(1-Methylethyl)benzenesulfonyl]-4-isopropoxy-5-(4-methylpiperazin-1-yl methyl)-1H-indole;
   1-(4-Fluorobenzenesulfonyl)-3-chloro-5-(piperazin-1-yl methyl)-1H-indole dihydrochloride;
   1-(2,4-Difluorobenzenesulfonyl)-3-chloro-5-(piperazin-1-yl methyl)-1H-indole dihydrochloride;
   and a pharmaceutically acceptable salt thereof.
2. The compound of claim 1, wherein said compound is 1-(4-Fluorobenzenesulfonyl)-5-(4-ethylpiperazin-1-yl methyl)-1H-indole dihydrochloride.
3. The compound of claim 1, wherein said compound is 1-(2-Bromobenzenesulfonyl)-5-(4-ethylpiperazin-1-yl methyl)-1H-indole dihydrochloride.
4. A compound, wherein said compound is 1-(4-Fluorobenzenesulfonyl)-3-chloro-5-(4-methylpiperazin-1-yl methyl)-1H-indole.
5. The compound of claim 1, wherein said compound is selected from the group consisting of:
   1-(4-Chlorobenzenesulfonyl)-5-(4-ethylpiperazin-1-yl methyl)-3-bromo-1H-indole dihydrochloride;
   1-(4-Chlorobenzenesulfonyl)-3-chloro-5-(4-methylpiperazin-1-yl methyl)-1H-indole;
   1-(4-Fluorobenzenesulfonyl)-3-chloro-5-(4-methylpiperazin-1-yl methyl)-1H-indole;
   1-(2,4-Difluorobenzenesulfonyl)-3-chloro-5-(4-methylpiperazin-1-yl methyl)-1H-indole dihydrochloride;
   1-(2-Chloro-5-trifluoromethylbenzenesulfonyl)-3-chloro-5-(4-methylpiperazin-1-yl methyl)-1H-indole dihydrochloride;
   1-(4-Fluorobenzenesulfonyl)-4-isopropoxy-5-(4-methylpiperazin-1-yl methyl)-1H-indole;
   1-[4-(1-Methylethyl)benzenesulfonyl]-4-isopropoxy-5-(4-methylpiperazin-1-yl methyl)-1H-indole;

1-(4-Fluorobenzenesulfonyl)-3-chloro-5-(piperazin-1-yl methyl)-1H-indole dihydrochloride;
1-(2,4-Difluorobenzenesulfonyl)-3-chloro-5-(piperazin-1-yl methyl)-1H-indole dihydrochloride; and a pharmaceutically acceptable salt thereof.

6. The compound of claim 5, wherein said compound is selected from the group consisting of:
1-(4-Chlorobenzenesulfonyl)-3-chloro-5-(4-methylpiperazin-1-yl methyl)-1H-indole;
1-(4-Fluorobenzenesulfonyl)-3-chloro-5-(4-methylpiperazin-1-yl methyl)-1H-indole;
1-(2,4-Difluorobenzenesulfonyl)-3-chloro-5-(4-methylpiperazin-1-yl methyl)-1H-indole dihydrochloride;
1-(2-Chloro-5-trifluoromethylbenzenesulfonyl)-3-chloro-5-(4-methylpiperazin-1-yl methyl)-1H-indole dihydrochloride;
1-(4-Fluorobenzenesulfonyl)-3-chloro-5-(piperazin-1-yl methyl)-1H-indole dihydrochloride;
1-(2,4-Difluorobenzenesulfonyl)-3-chloro-5-(piperazin-1-yl methyl)-1H-indole dihydrochloride;
1-(4-Chlorobenzenesulfonyl)-5-(4-ethylpiperazin-1-yl methyl)-3-bromo-1H-indole dihydrochloride; and a pharmaceutically acceptable salt thereof.

7. The compound of claim 5, wherein said compound is selected from the group consisting of:
1-(4-Chlorobenzenesulfonyl)-3-chloro-5-(4-methylpiperazin-1-yl methyl)-1H-indole;
1-(4-Fluorobenzenesulfonyl)-3-chloro-5-(4-methylpiperazin-1-yl methyl)-1H-indole;
1-(2,4-Difluorobenzenesulfonyl)-3-chloro-5-(4-methylpiperazin-1-yl methyl)-1H-indole dihydrochloride;
1-(2-Chloro-5-trifluoromethylbenzenesulfonyl)-3-chloro-5-(4-methylpiperazin-1-yl methyl)-1H-indole dihydrochloride;
1-(4-Fluorobenzenesulfonyl)-3-chloro-5-(piperazin-1-yl methyl)-1H-indole dihydrochloride;
1-(2,4-Difluorobenzenesulfonyl)-3-chloro-5-(piperazin-1-yl methyl)-1H-indole dihydrochloride; and a pharmaceutically acceptable salt thereof.

8. The compound of claim 1, wherein said compound is selected from the group consisting of:
1-(4-Chlorobenzenesulfonyl)-5-(4-ethylpiperazin-1-yl methyl)-1H-indole dihydrochloride;
1-(4-Bromobenzenesulfonyl)-5-(4-ethylpiperazin-1-yl methyl)-1H-indole dihydrochloride; and
1-(4-Chlorobenzenesulfonyl)-5-(4-ethylpiperazin-1-yl methyl)-3-bromo-1H-indole dihydrochloride.

9. The compound of claim 1, wherein said compound is 1-(4-Chlorobenzenesulfonyl)-5-(4-ethylpiperazin-1-yl methyl)-1H-indole dihydrochloride.

10. The compound of claim 1, wherein said compound is 1-(4-Bromobenzenesulfonyl)-5-(4-ethylpiperazin-1-yl methyl)-1H-indole dihydrochloride.

11. The compound of claim 1, wherein said compound is 1-(4-Chlorobenzenesulfonyl)-5-(4-ethylpiperazin-1-yl methyl)-3-bromo-1H-indole dihydrochloride.

12. The compound of claim 1, wherein said compound is 1-(4-Chlorobenzenesulfonyl)-3-chloro-5-(4-methylpiperazin-1-yl methyl)-1H-indole, or a pharmaceutically acceptable salt thereof.

13. The compound of claim 1, wherein said compound is 1-(2,4-Difluorobenzenesulfonyl)-3-chloro-5-(4-methylpiperazin-1-yl methyl)-1H-indole dihydrochloride.

14. The compound of claim 1, wherein said compound is 1-(2-Chloro-5-trifluoromethylbenzenesulfonyl)-3-chloro-5-(4-methylpiperazin-1-yl methyl)-1H-indole dihydrochloride.

15. The compound of claim 1, wherein said compound is 1-(4-Fluorobenzenesulfonyl)-4-isopropoxy-5-(4-methylpiperazin-1-yl methyl)-1H-indole, or a pharmaceutically acceptable salt thereof.

16. The compound of claim 1, wherein said compound is 1-[4-(1-Methylethyl)benzenesulfonyl]-4-isopropoxy-5-(4-methylpiperazin-1-yl methyl)-1H-indole, or a pharmaceutically acceptable salt thereof.

17. The compound of claim 1, wherein said compound is 1-(4-Fluorobenzenesulfonyl)-3-chloro-5-(piperazin-1-yl methyl)-1H-indole dihydrochloride.

18. The compound of claim 1, wherein said compound is 1-(2,4-Difluorobenzenesulfonyl)-3-chloro-5-(piperazin-1-yl methyl)-1H-indole dihydrochloride.

19. A method for the treatment of Alzheimer's disease by enhancing cognition and memory in an Alzheimer's patient in need thereof, which comprises the step of providing to said patient the compound as claimed in claim 2.

20. A method for the treatment of Alzheimer's disease by enhancing cognition and memory in an Alzheimer's patient in need thereof, which comprises the step of providing to said patient the compound as claimed in claim 3.

21. A method for the treatment of Alzheimer's disease by enhancing cognition and memory in an Alzheimer's patient in need thereof, which comprises the step of providing to said patient the compound as claimed in claim 4.

* * * * *